US012357741B2

United States Patent
Allard et al.

(10) Patent No.: US 12,357,741 B2
(45) Date of Patent: Jul. 15, 2025

(54) PORTABLE CENTRIFUGE DEVICE AND METHOD OF USE

(71) Applicant: ABC Med Tech Corp., Golden, CO (US)

(72) Inventors: Randall Allard, Golden, CO (US); Polly Allard, Golden, CO (US); William Bradley Lydens, Seattle, WA (US)

(73) Assignee: ABC Med Tech Corp., Golden, CO (US)

( * ) Notice: Subject to any disclaimer, the term of this patent is extended or adjusted under 35 U.S.C. 154(b) by 0 days.

(21) Appl. No.: 18/619,972

(22) Filed: Mar. 28, 2024

(65) Prior Publication Data

US 2024/0238498 A1    Jul. 18, 2024

Related U.S. Application Data

(62) Division of application No. 16/815,430, filed on Mar. 11, 2020, now Pat. No. 11,964,092.

(60) Provisional application No. 62/816,873, filed on Mar. 11, 2019.

(51) Int. Cl.
| | |
|---|---|
| *A61M 1/36* | (2006.01) |
| *B04B 1/02* | (2006.01) |
| *B04B 7/02* | (2006.01) |
| *B04B 9/04* | (2006.01) |
| *B04B 9/08* | (2006.01) |

(52) U.S. Cl.
CPC ............ *A61M 1/3693* (2013.01); *B04B 1/02* (2013.01); *B04B 7/02* (2013.01); *B04B 9/04* (2013.01); *B04B 9/08* (2013.01)

(58) Field of Classification Search
CPC .......... B04B 5/0421; B04B 9/00; B04B 9/08; B04B 1/02; B04B 7/02; B04B 9/04; B04B 15/00; A61M 1/3693; A61M 2202/0427; B01F 2101/20; B01F 27/88; B01F 27/90; B01F 35/32005
USPC .................................. 494/10, 20, 83–85, 11
See application file for complete search history.

(56) References Cited

U.S. PATENT DOCUMENTS

| | | | | |
|---|---|---|---|---|
| 3,567,113 | A * | 3/1971 | Stansell | B04B 5/00 494/84 |
| 5,242,370 | A * | 9/1993 | Silver | B04B 13/00 422/918 |
| 5,924,972 | A * | 7/1999 | Turvaville | B04B 5/0414 494/12 |
| 7,645,223 | B2 * | 1/2010 | Namkoong | B01L 3/5021 494/84 |
| 8,986,185 | B2 * | 3/2015 | Del Vecchio | B04B 5/0421 494/16 |
| 9,839,921 | B2 * | 12/2017 | Yarina | B04B 9/08 |
| 10,335,803 | B2 * | 7/2019 | Yarina | B04B 9/00 |
| 10,792,675 | B2 * | 10/2020 | Yarina | B04B 9/08 |
| 11,964,092 | B2 * | 4/2024 | Allard | A61M 1/3693 |

(Continued)

*Primary Examiner* — Charles Cooley

(74) *Attorney, Agent, or Firm* — BrainSpark Associates, LLC

(57) ABSTRACT

A portable centrifuge having a housing containing a rotational mechanism and a centrifugal container having a longitudinal axis. The rotational mechanism has a circuit including an electrical motor, a switch, and an internal electrical power source. The centrifugal container is operably connected to the rotational mechanism through the housing, and is rotatable about the longitudinal axis. The centrifuge is portable and is for single use.

18 Claims, 33 Drawing Sheets

(56) References Cited

U.S. PATENT DOCUMENTS

| | | | |
|---|---|---|---|
| 2011/0130263 A1* | 6/2011 | Del Vecchio | B04B 9/08 494/20 |
| 2012/0309636 A1* | 12/2012 | Gibbons | C12Q 1/6809 435/6.12 |
| 2013/0265417 A1* | 10/2013 | Rust | G01N 33/491 494/20 |
| 2014/0057770 A1* | 2/2014 | Holmes | B04B 15/02 494/10 |
| 2016/0030952 A1* | 2/2016 | Yarina | B04B 9/02 435/5 |
| 2018/0065128 A1* | 3/2018 | Yarina | B04B 5/0421 |
| 2019/0314829 A1* | 10/2019 | Yarina | B04B 5/0421 |
| 2020/0289738 A1* | 9/2020 | Allard | B01F 27/88 |
| 2021/0316317 A1* | 10/2021 | Schaff | B04B 7/08 |
| 2022/0257841 A1* | 8/2022 | Allard | A61L 2/10 |
| 2023/0381792 A1* | 11/2023 | Allard | B04B 7/02 |
| 2024/0238498 A1* | 7/2024 | Allard | B04B 1/02 |

* cited by examiner

FIG. 27
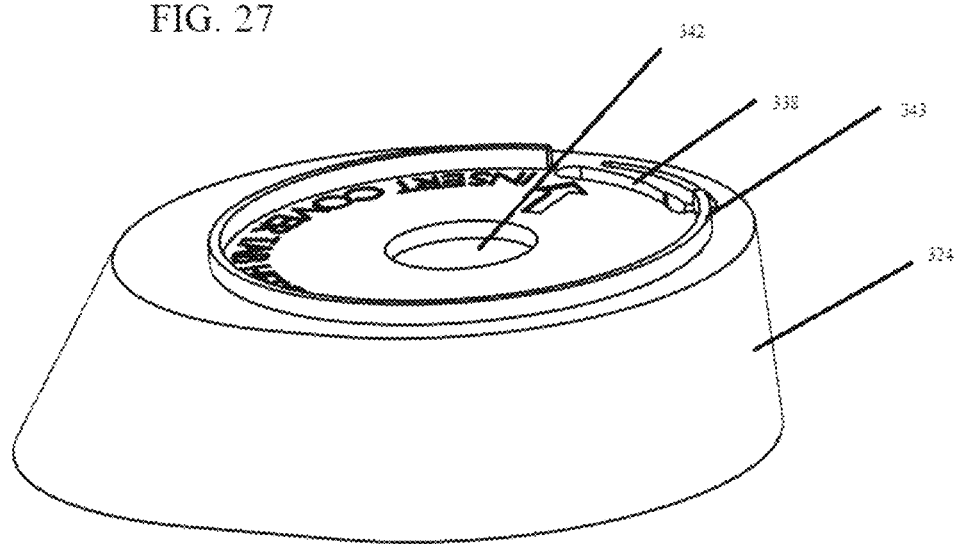
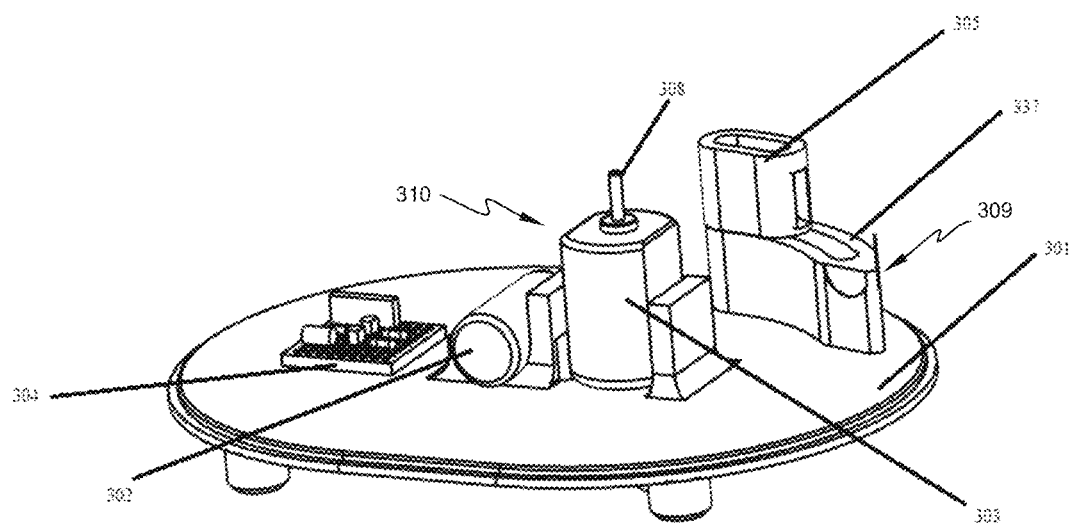

PORTABLE CENTRIFUGE DEVICE AND METHOD OF USE

CROSS REFERENCE TO RELATED APPLICATIONS

This application is a divisional of U.S. application Ser. No. 16/815,430 filed on Mar. 11, 2020, entitled "Portable Centrifuge and Method of Use," that claims benefit to U.S. Provisional Application No. 62/816,873, filed Mar. 11, 2019, entitled "PRP Centrifuge and Method of Use," which both applications are incorporated herein in their entireties.

TECHNICAL FIELD

The present invention generally relates to centrifugal systems used to separate blood and to produce platelet rich plasma (PRP). More particularly, the present invention relates to a portable and centrifugal system for use in a surgical environment.

BACKGROUND INFORMATION

Currently systems used to separate blood and to produce platelet rich plasma (PRP) commonly involve a centrifuge. Blood separation centrifuges are based on two basic designs: 1) the standard lab centrifuge, where a vessel is placed inside a chamber and then spun at high speeds to induce separation; and 2) the Latham Bowl designed centrifuge, where blood is injected into a bowl with angled walls and then spun at high speeds to induce separation.

Problems exist with current commercially available centrifuges, including difficulty sterilizing the electrical components, in particular circuitry and power components and cell damage due to excessive steps with handling of the blood.

Thus, a need exists for a blood separation system and process that can be used in a sterile environment and that minimizes the number of handling and processing steps.

SUMMARY OF THE INVENTION

In one aspect, a centrifuge is provided having a housing containing a rotational mechanism and a centrifugal container having a longitudinal axis. The rotational mechanism has a circuit including an electrical motor, a switch, and an internal electrical power source. The centrifugal container is operably connected to the rotational mechanism through the housing, and is rotatable about the longitudinal axis. The centrifuge is portable.

Provided in another aspect, is a method including providing a centrifuge having a housing with a rotational mechanism within, a centrifugal container having a longitudinal axis, and a protective cover. The protective cover includes a circumferential sidewall extending from a top end to a base end having an opening, a cover longitudinal axis, and an activation tab extending from the base end of the circumferential sidewall. The rotational mechanism has a circuit including an electrical motor, a switch, and an internal electrical power source. The centrifugal container is operably connected to the rotational mechanism through the housing, and is rotatable about the longitudinal axis. The protective cover covers the centrifugal container and the activation tab extends into the housing and is operably connected to the switch. The centrifuge is sterile and sealed in packaging. The packaging and the protective cover are removed. Fluid is introduced into the centrifugal container and the protective cover is replaced such that the activation tab is inserted into the switch. The protective cover is turned about the cover longitudinal axis, moving the activation tab, and thus, the switch to activate the electrical motor. The electrical motor rotates the centrifugal container, separating the fluid into constituent components. The protective cover is removed from the centrifuge and a desired constituent component is removed.

These, and other objects, features and advantages of this invention will become apparent from the following detailed description of the various aspects of the invention taken in conjunction with the accompanying drawings.

BRIEF DESCRIPTION OF THE DRAWINGS

The present invention will be understood more fully from the detailed description given hereinafter and from the accompanying drawings of certain embodiment of the present invention, which, however, should not be taken to limit the invention, but are for explanation and understanding only.

FIG. 27 is a perspective view of the of FIG. 26, with the powertrain cover removed, in accordance with an aspect of the present invention;

DETAILED DESCRIPTION OF THE INVENTION

There is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The systems, methods, and apparatus described are directed to a centrifugal device for use in a sterile environment.

The following description references systems, methods, and apparatuses for a centrifugal device for separating blood (e.g. venous blood or bone marrow aspirate) into blood plasma, platelet rich plasma, platelet poor plasma, and red blood cells and extracting the platelet rich plasma. The following description also references systems, methods, and apparatuses for a centrifugal device for separating blood or bone cement preparation without having to leave the surgical environment. However, those possessing an ordinary level of skill in the relevant art will appreciate that other fluids, mixtures, slurries, and liquids are suitable for use with the foregoing systems, methods and apparatuses. Furthermore, those possessing an ordinary level of skill in the relevant art will appreciate that this device may be used outside the surgical environment, and in sterile and non-sterile environments. Likewise, the various figures, steps, procedures and work-flows are presented only as an example and in no way limit the systems, methods or apparatuses described to perform their respective tasks and/or outcomes in different time-frames or orders. The teachings of the present invention may be applied to medical processes for viruses, cell cultures, proteins, nucleic acids, bone cement preparation, and polymers, and may be implemented in other processes that have similar separation considerations.

Figure 1:
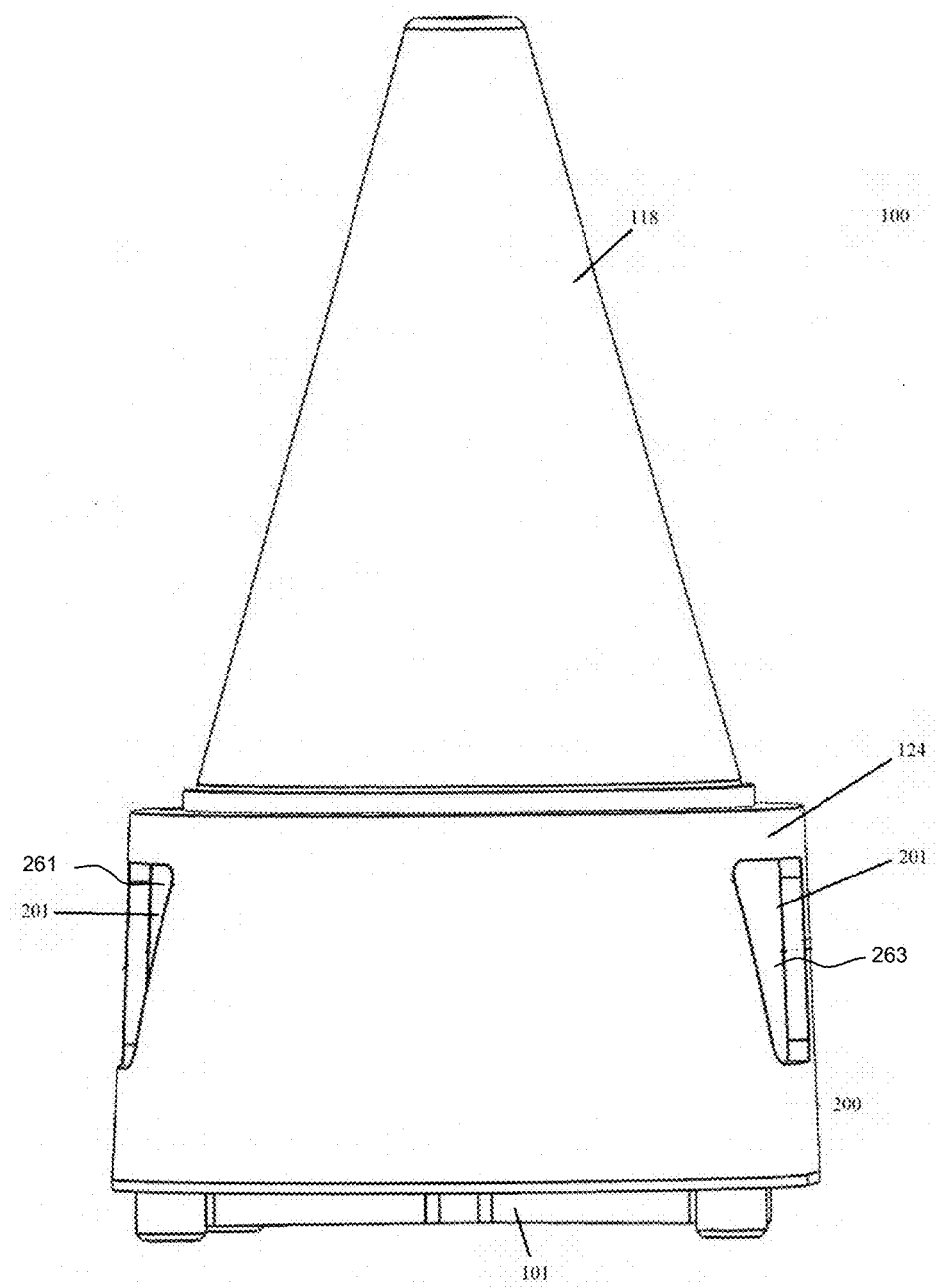
FIG. 1 is a front view of a centrifuge, in accordance with an aspect of the present invention.
Figure 2:
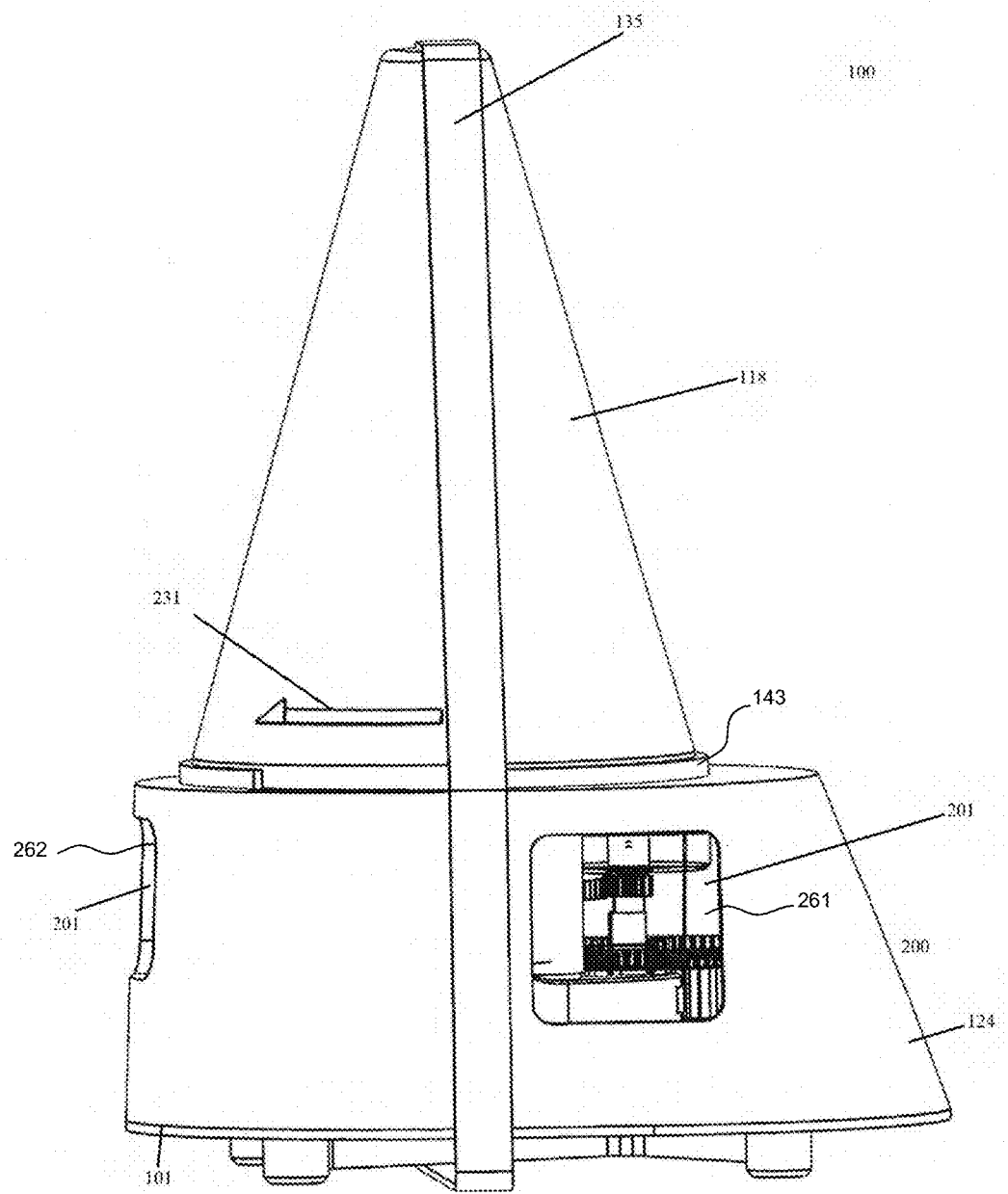
FIG. 2 is a side view of the centrifuge of FIG. 1, in accordance with an aspect of the present invention.

Referring to the drawings, wherein like reference numerals are used to indicate like or analogous components throughout the several views, and with particular reference to FIGS. 1-2, one embodiment of a centrifuge 100 is shown, fully assembled and sealed. The centrifuge 100 may be, for example, separate blood to obtain platelet rich plasma. The centrifuge 100 may include, for example, a protective cover 118, a powertrain base 200, and a travel tape 135. The travel tape 135 may be removable and may be placed, for example, about centrifuge 100 to keep the protective cover 118 on the powertrain base 200 prior to use, to maintain sterility. The centrifuge 100 may be sterilized prior to use and may be usable in a sterile environment, such as an operating room theater. The powertrain base 200 may have a powertrain cover 124, a plurality of base holes 201 (e.g. there may be a first side opening 161, a rear opening 162, and a second side opening 163), and a baseplate 101. The protective cover 118 may be positioned on the powertrain base 200 and positioned within a protective cover track 143.

Figure 3:
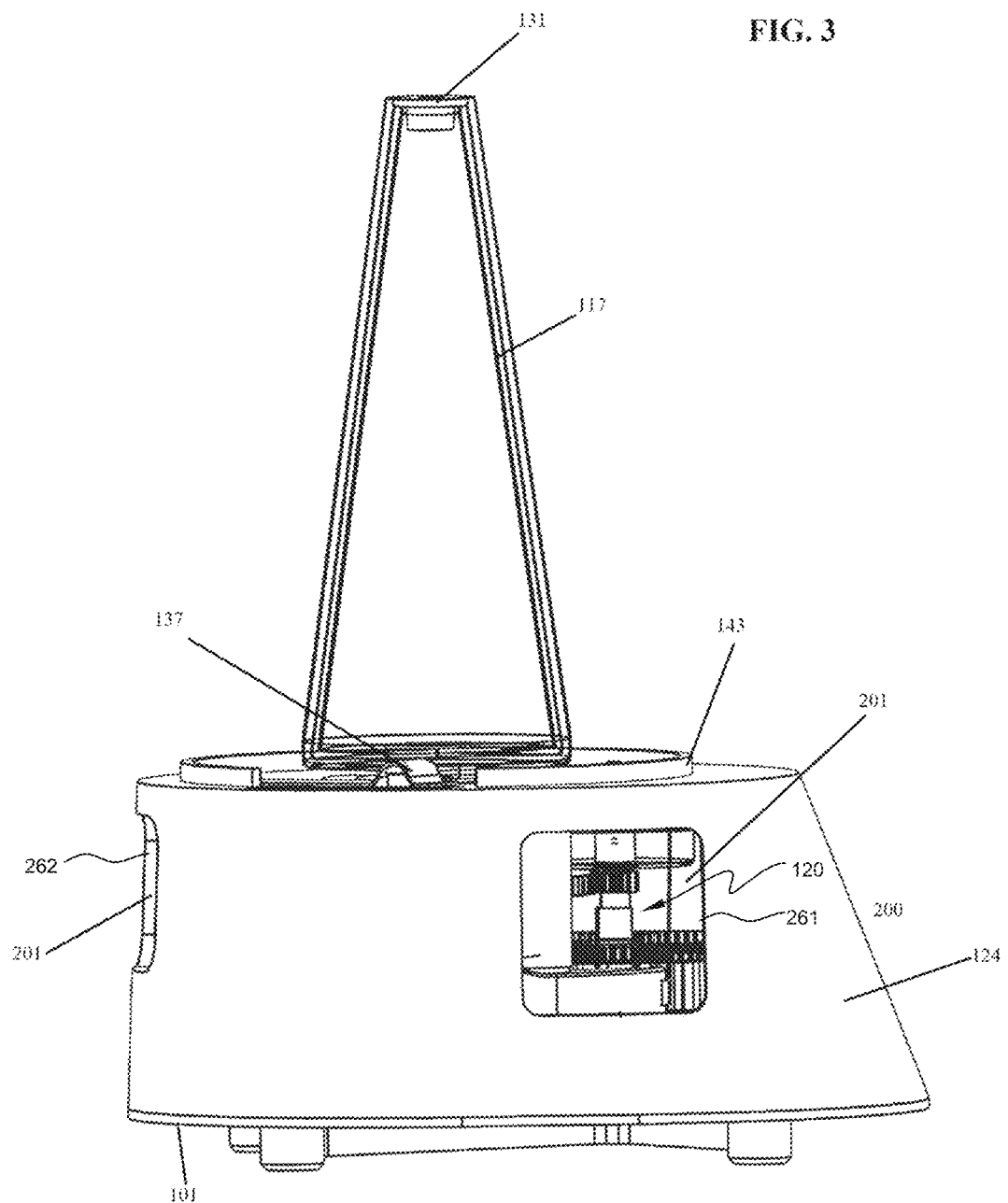
FIG. 3 is a side view of the centrifuge of FIG. 1 with a container, in accordance with an aspect of the present invention.

Referring to FIG. 3, the powertrain base 200 is depicted with a container 117. The container 117 may be hollow and have a stopper 131, with the stopper 131 positioned, for example, into or at a top opening 142. The stopper 131 may have a stopper opening 232. The container 117 may be, for example, sized to hold from approximately 20 ml up to approximately 100 ml of blood. More specifically, the container 117 may be, for example, sized from approximately 30 to approximately 50 ml. The container 117 is shown as being clear or transparent, because it makes it easy to see layers of the separated blood and to determine which is the PRP for withdrawal. The container 117 may also be opaque. The stopper opening 232 may also be referred to as a siphon port.

Continuing with FIG. 3, the powertrain base 200 may also include, for example, a travel pin 137. A powertrain 120 may be accessible through the first side opening 161 of base holes 201. The rear opening 162 of base holes 201 may be in the back of centrifuge 100. The travel pin 137 may be removable and may be used to, for example, prevent the centrifuge 100 from activation before use is required. The travel pin 137 may be a single peg or pin or there may be multiple pegs or pins that may prevent the powertrain 120 from activating.

Generally referring to FIGS. 1-3, the protective cover 118 may cover the container 117 and be seated within the protective cover track 143. The container 117 may be, for example, conical or any three-dimensional shape, including but not limited to cylinders and spheres. The protective cover 118 may be of a similar or a different shape to the container 117. However, the protective cover 118 may be, for example, of a suitable size and shape to cover or substantially cover the container 117.

Figure 4:
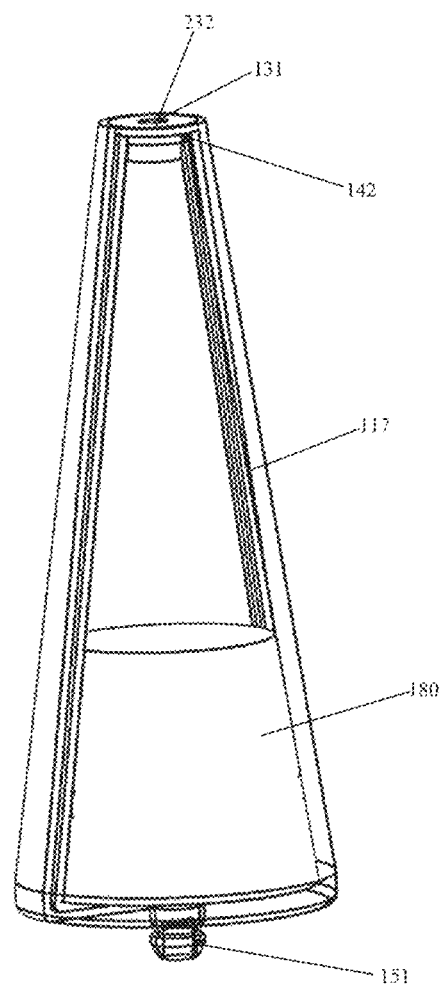
FIG. 4 is a cut-away view of the container of FIG. 3, in accordance with an aspect of the present invention.
Figure 5:
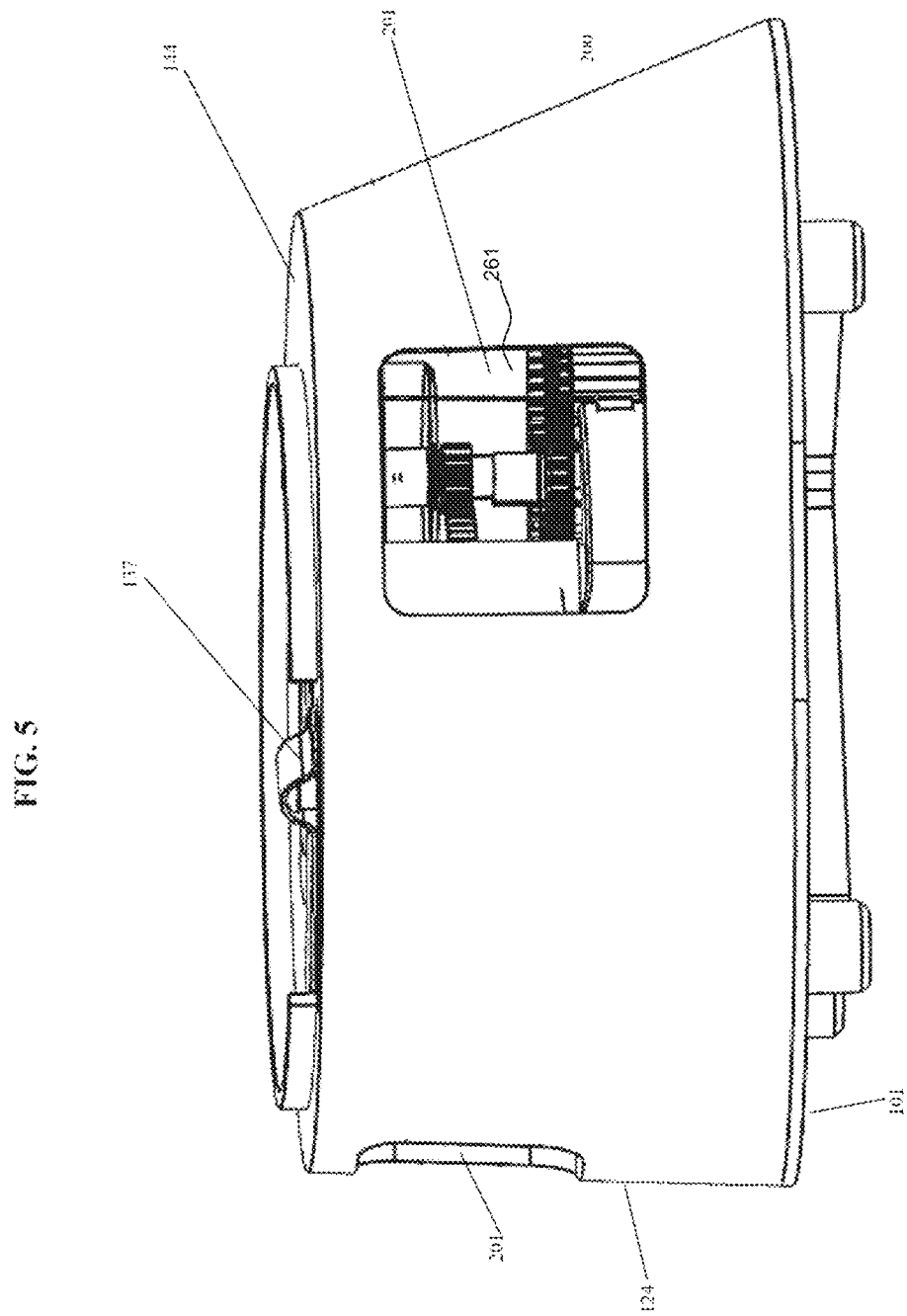
FIG. 5 is a side view of a base for the centrifuge of FIG. 1, in accordance with an aspect of the present invention.
Figure 6:
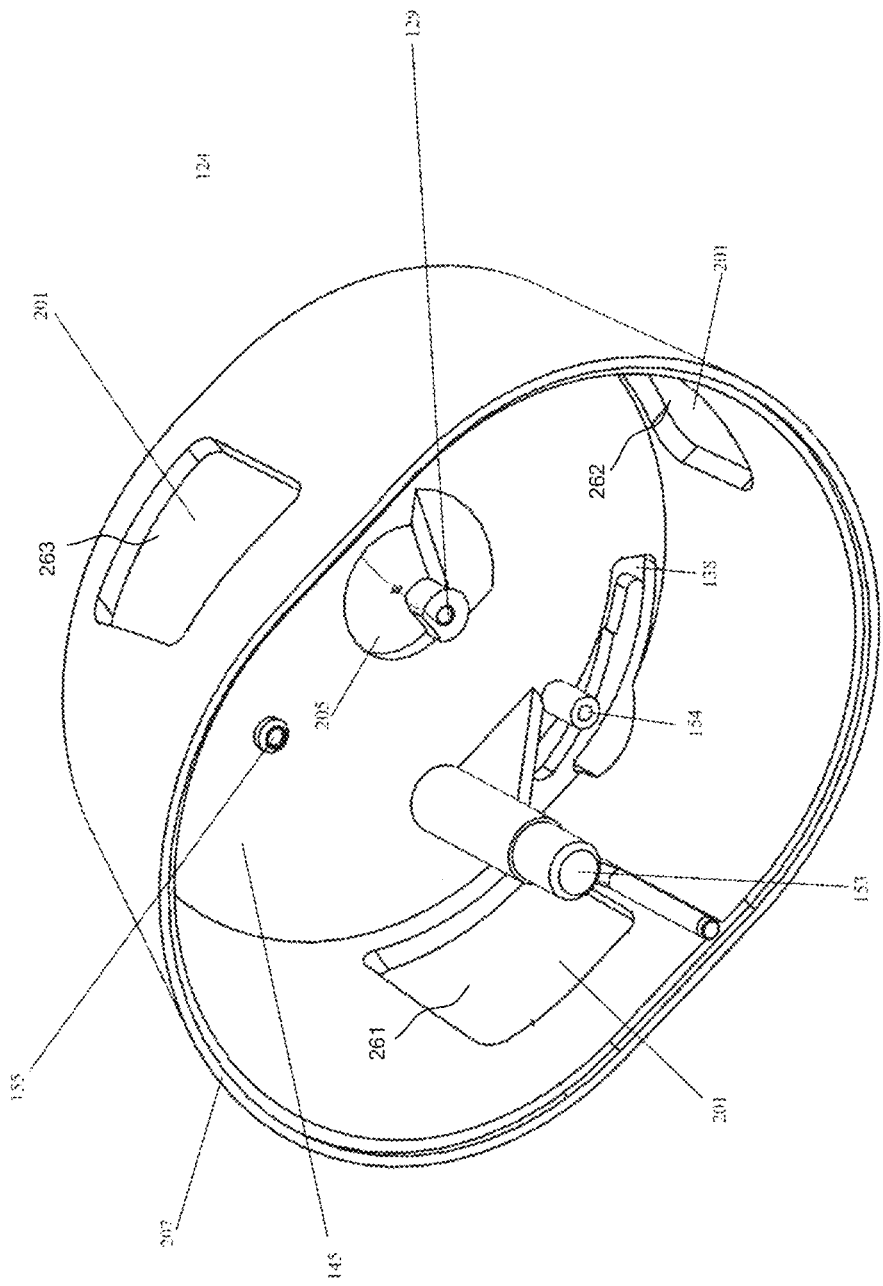
FIG. 6 is a bottom view of a powertrain cover of the centrifuge of FIG. 1, in accordance with an aspect of the present invention.
Figure 7:
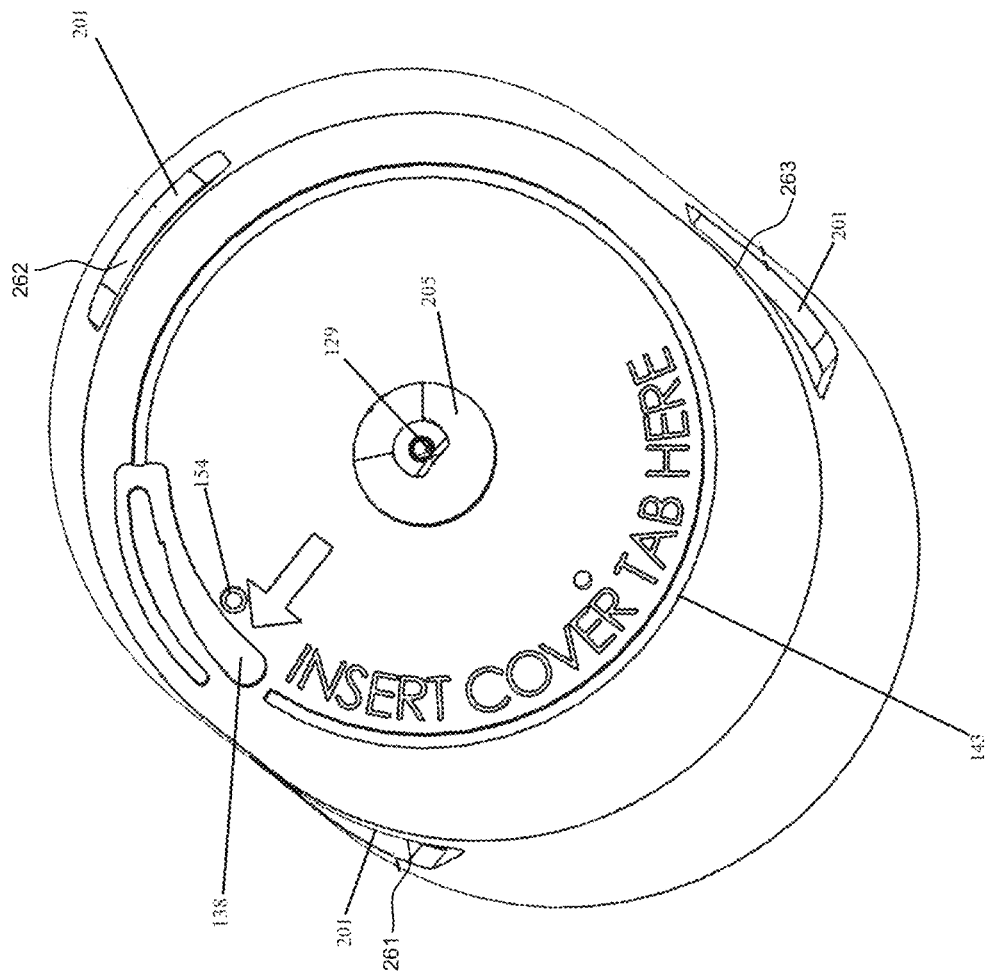
FIG. 7 is a top view of a powertrain cover of the centrifuge of FIG. 1, in accordance with an aspect of the present invention.
Figure 8:
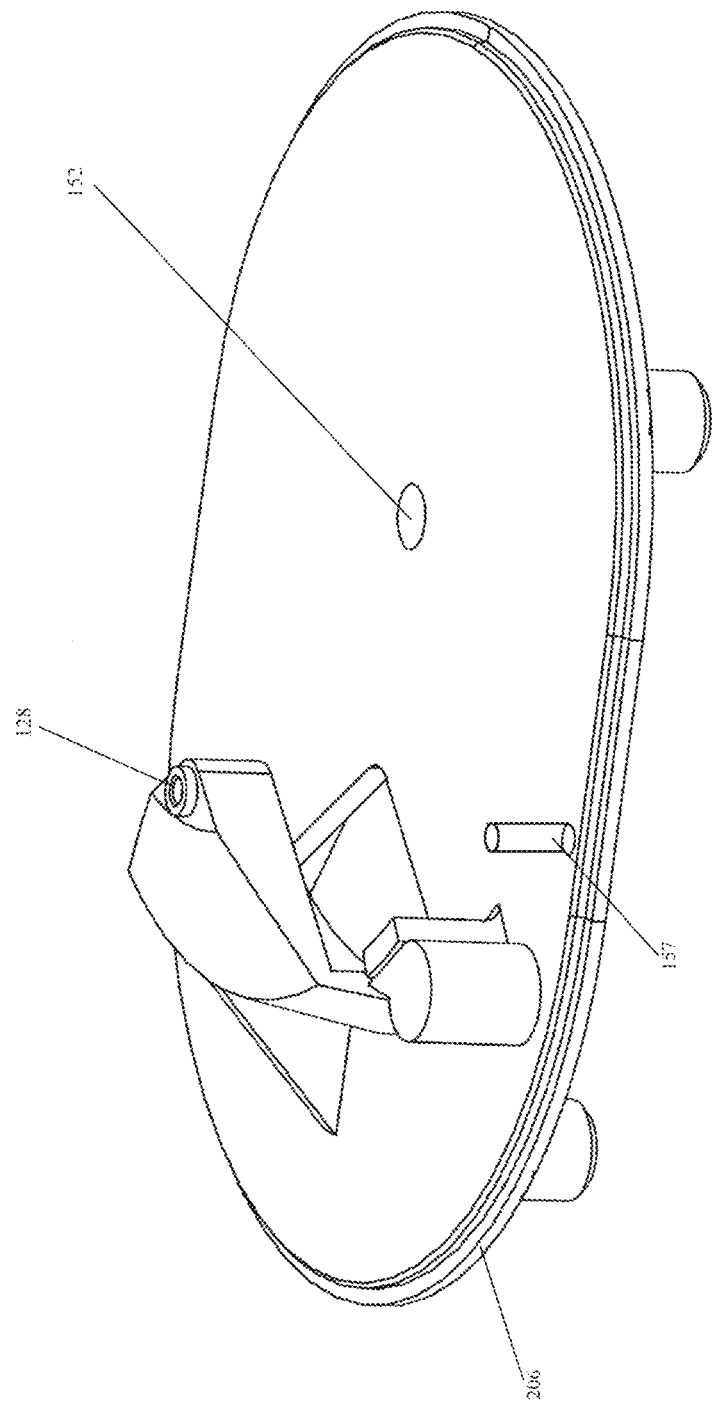
FIG. 8 is a perspective view of a baseplate of the centrifuge of FIG. 1, in accordance with an aspect of the present invention.

FIG. 4 shows the container 117 with a container powertrain connector 151 and the stopper 131 inserted into the top opening 142. Liquid in the form of the blood 180 may be inside the container 117. As the container 117 is part of the centrifuge 100 and therefore spun at a speed of at least 3000 rpm, the shape of the container 117 may be such so as to keep fluid contained within the container 117 and to encourage blood separation. While the container 117 may be any shape, a configuration with sloped side walls and with a narrower top and wider bottom, may aid in keeping the blood 180 within the container 117 and may also force heavier blood constituents to the bottom while lighter blood constituents progress to the top.

When activated, the centrifuge 100 may spin the container 117 at speeds that may range from 3000 rpm to 20,000 rpm for a period of at least one minute, with the spin time ranging from 1-3 minutes. To separate the blood 180 and to obtain the platelet rich plasma (PRP) 182, the container 117 may commonly spin, for example, within a range of rotational speeds from approximately 4000 rpm-15000 rpm.

As depicted in FIGS. 5-8, the powertrain base 200 has the powertrain cover 124 and the baseplate 101, that may act as a housing for the powertrain 120. The powertrain cover 124 has base holes 201, for example, the first side opening 161, the rear opening 162, and the second side opening 163. The powertrain cover 124 may also have a powertrain cover top 144, having an interior powertrain cover surface 145, the protective cover track 143, and a container base opening 205 through the powertrain cover top 144. Extending from the interior powertrain cover surface 145 and extending to approximately align with a center for the container base opening 205, is a second shaft support 129. Extending through the powertrain cover top 144 and from the interior powertrain cover surface 145 may be a cylindrical hole or tube through which the travel pin 137 may be placed. Also extending through the powertrain cover top 144 may be a trigger slot 138 and a travel pin slot 154. Further extending from the interior powertrain cover surface 145 may be a pawl support 153.

The powertrain cover 124 may connect to the baseplate 101 at a baseplate edge 206 where, for example, the powertrain cover 124 may have a powertrain cover edge 207 which may connect to the baseplate edge 206. The baseplate 101 may also have a first base support 128, a base ground post 157, and a baseplate wind shaft connector hole 152.

Figure 9:
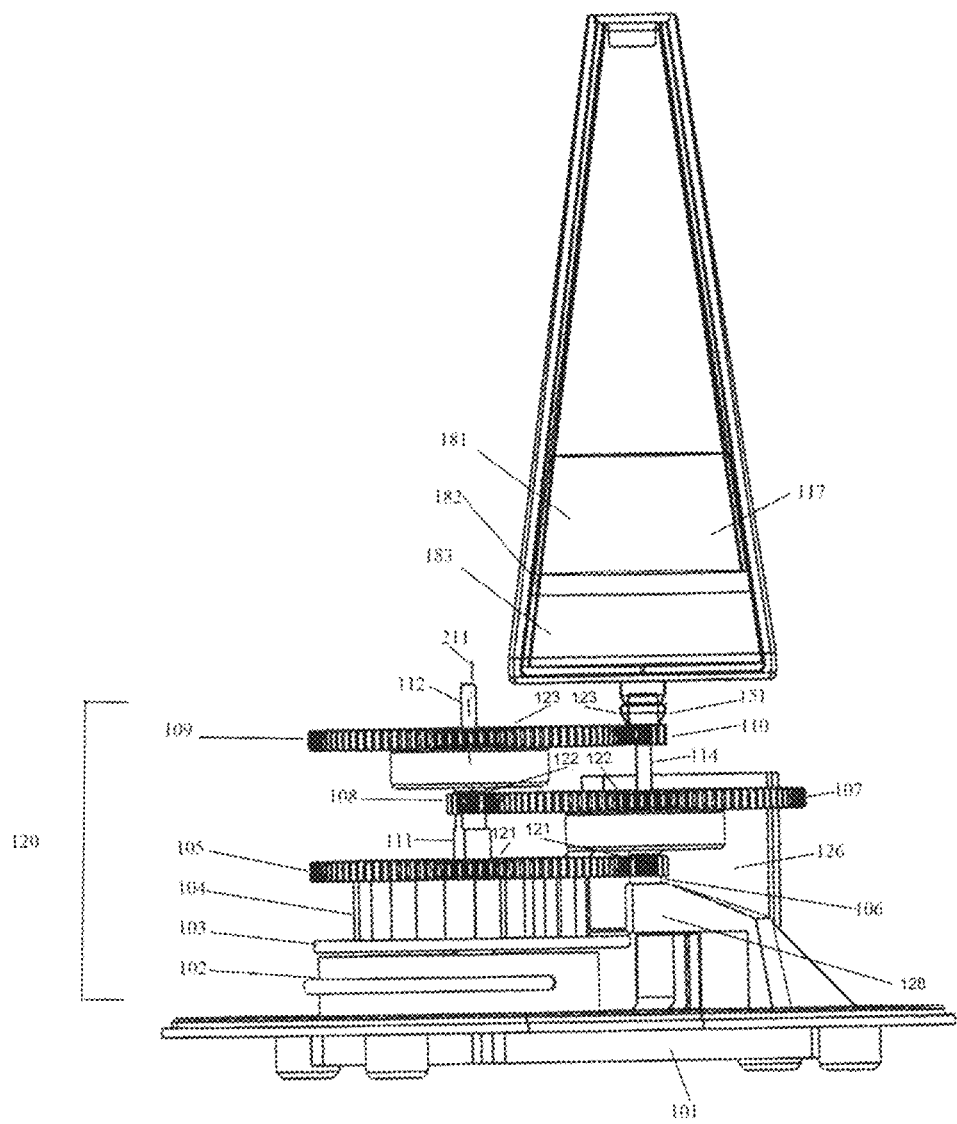
FIG. 9 is a side view of the powertrain and container of the centrifuge of FIG. 1, in accordance with an aspect of the present invention.

Shown in FIG. 9 is the baseplate 101 connected to a powertrain 120, with the powertrain 120 connected to the container 117.

Referring to FIGS. 9-13, the powertrain 120 may be mechanically powered, using for example, a coil spring motor 102, a first gear pair 121, a second gear pair 122, and a third gear pair 123 to rotatably move the container 117. Components of the powertrain 120 may include, for example, the coil spring motor 102, a wind shaft 111, a coil spring washer 103, a ratchet gear 104, a first large gear 105, a first small gear 106, a first small gear bushing 113, a second large gear bushing 115, a second large gear 107, a second small gear 108, a first shaft 112, a first bushing 113, a third large gear bushing 116, a third large gear 109, a third small gear 110, and a second shaft 114. The first small gear 106 and the second small gear 108 may each be referred to as "a pinion". The third small gear 110 may also be referred to as a "spindle gear". While the first small gear bushing 113 and the second large gear bushing 115 are shown in this embodiment, there may be other embodiments where a single bushing may be used to connect the first small gear 106 to the second large gear 107. Bushings may be used to adjust gear spacing and to facilitate the connection between vertically aligned gears. There may also be embodiments where no bushings are used to connect the first small gear 106 to the second large gear 107 and to connect the second small gear 108 to the third large gear 109. The first small gear 106 and second large 107 gear may be molded as a complete unit. The second small gear 108 and the third large gear 109 may be molded as a complete unit. The gears may be arranged in meshing pairs. The first gear pair 121 may be, for example, the first large gear 105 and the first small gear 106. The second gear pair 122 may be, for example, the second large gear 107 and the second small gear 108. The third gear pair 123 may be, for example, the third large gear 109 and the third small gear 110.

Figure 14:
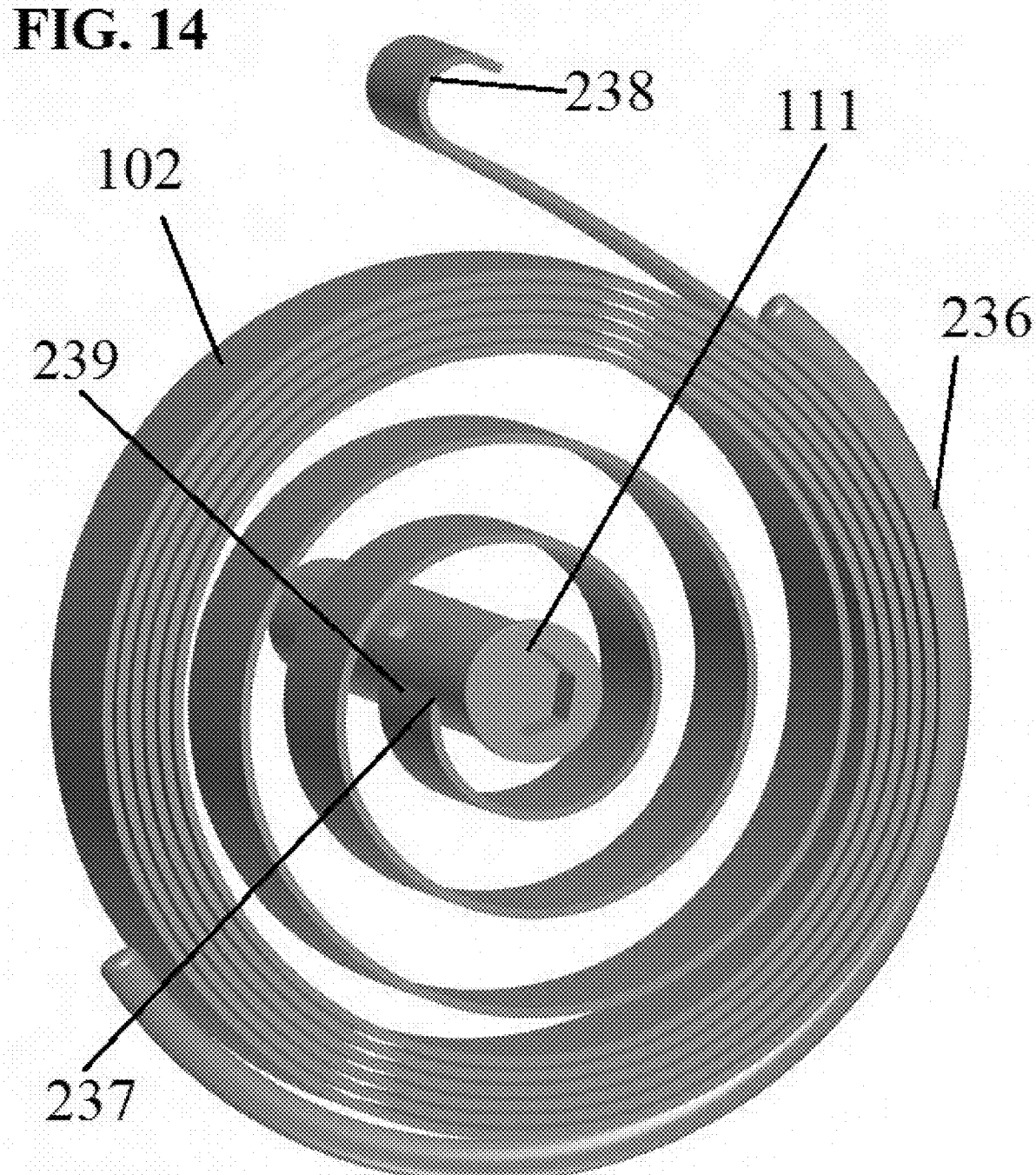
FIG. 14 is a bottom perspective view of the coil spring motor and wind shaft of the powertrain of FIG. 10, in accordance with an aspect of the present invention.

FIG. 14 shows the coil spring motor 102 threaded into the wind shaft 111 by placing a coil spring first end 237 into a coil spring connector 239. A coil spring second end 238 is depicted as being free. Coil spring restraint 236 is also shown.

Figure 15:
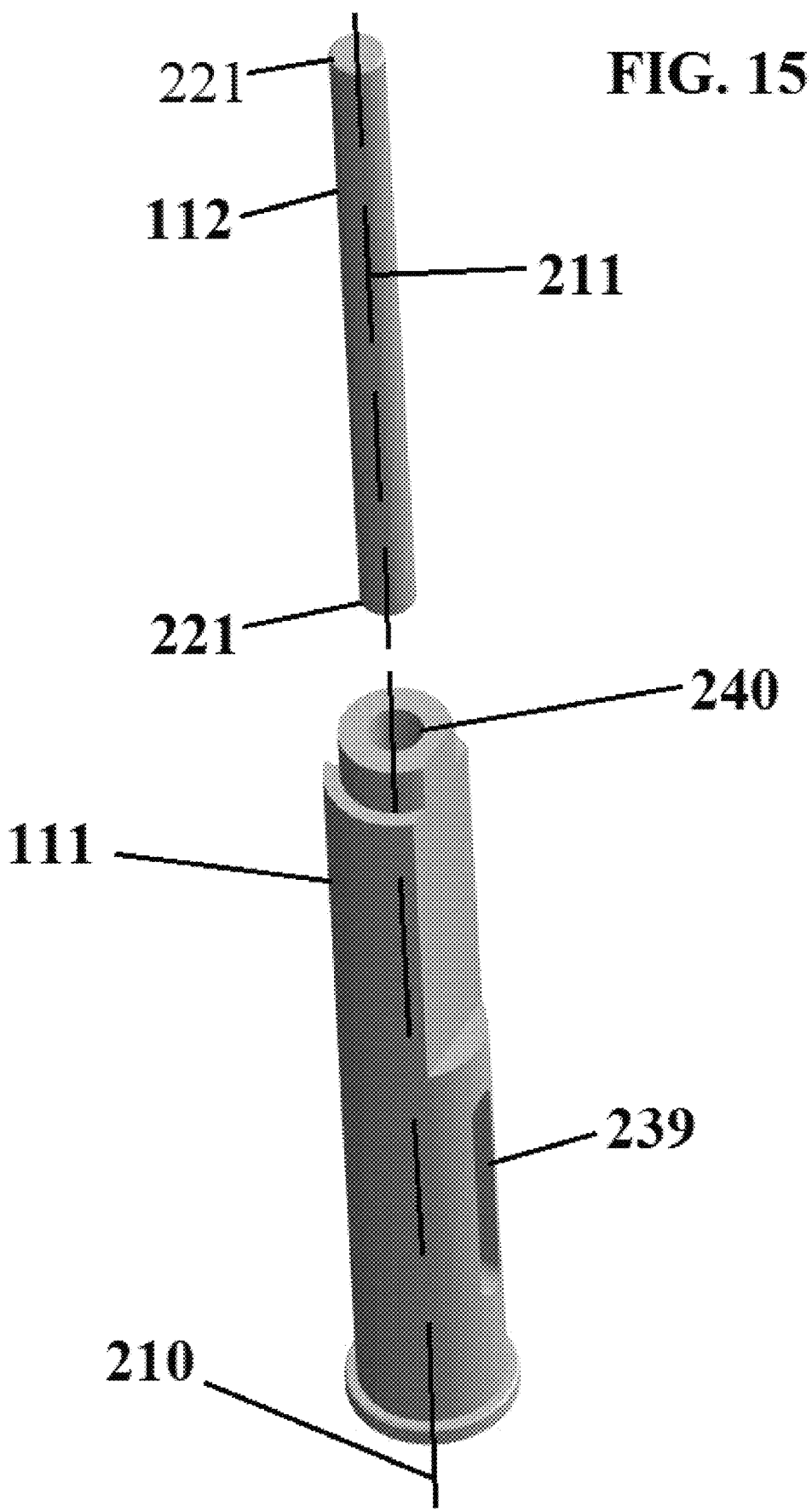
FIG. 15 is an exploded view of the wind shaft and first shaft of the powertrain of FIG. 10, in accordance with an aspect of the present invention.

FIG. 15 shows the wind shaft 111 having a wind shaft aperture 240, a longitudinal axis 210, and the coil spring connector 239. The first shaft 112 is shown having a first shaft first end 221, a first shaft longitudinal axis 211, and a first shaft second end 222. The first shaft second end is shown positioned above the wind shaft aperture 240.

Figure 16:
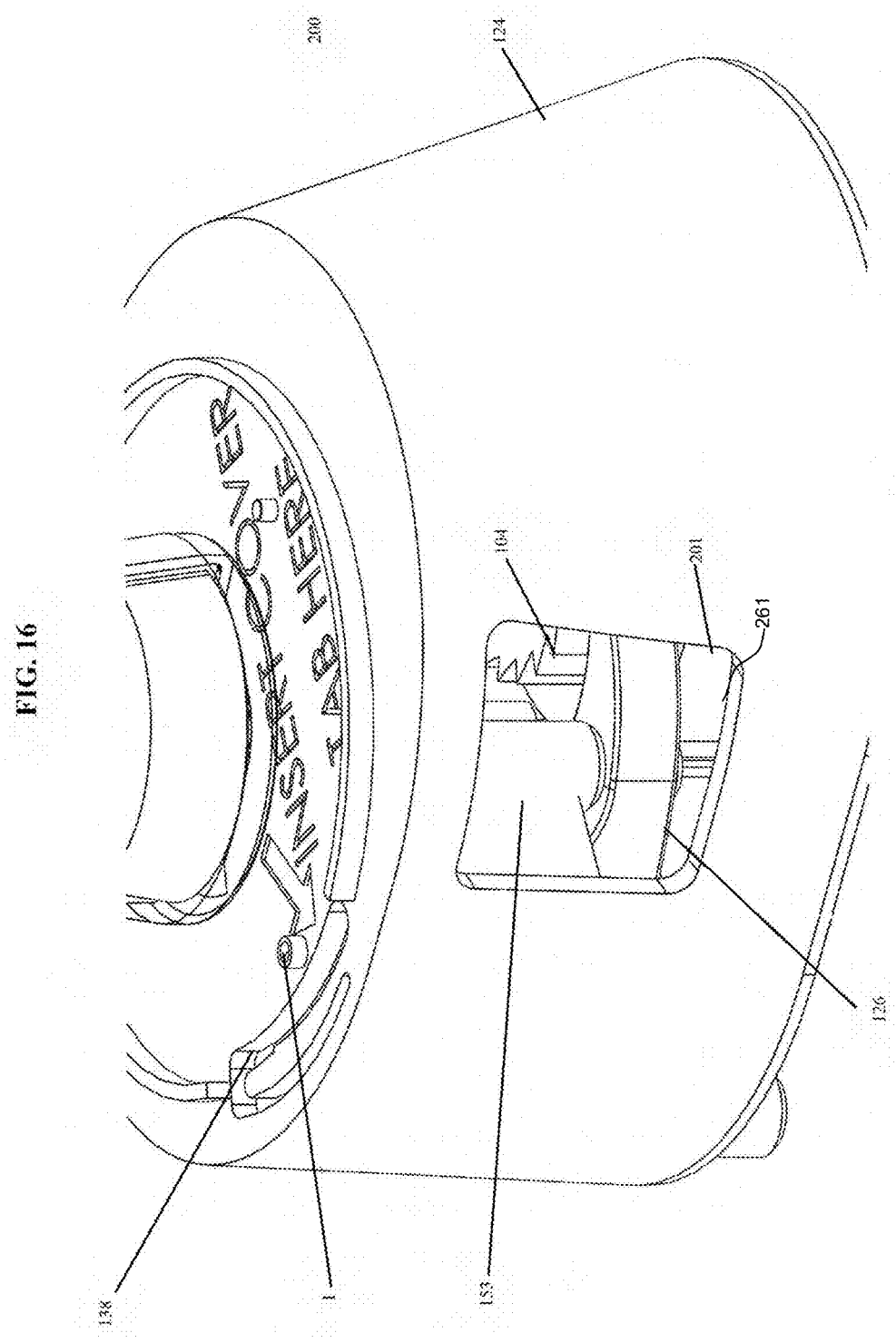
FIG. 16 is a perspective view of the powertrain base with a pawl and pawl support connection of the centrifuge of FIG. 1, in accordance with an aspect of the present invention.

Referring to FIG. 16, the powertrain base 200 may have, for example, the powertrain cover 124, the trigger slot 138, the cover track 143, and first side opening 161 of the base holes 201, with a pawl 126 partially visible through the first side opening, and the pawl 126 connected to the pawl support 153, such that the pawl 126 may pivot about the pawl support 153. An alternative to using the pawl 126 pivoting about the pawl support 153 for preventing the ratchet gear 104 from moving may be, for example, a removable pin, or a removable slat.

Figure 17:
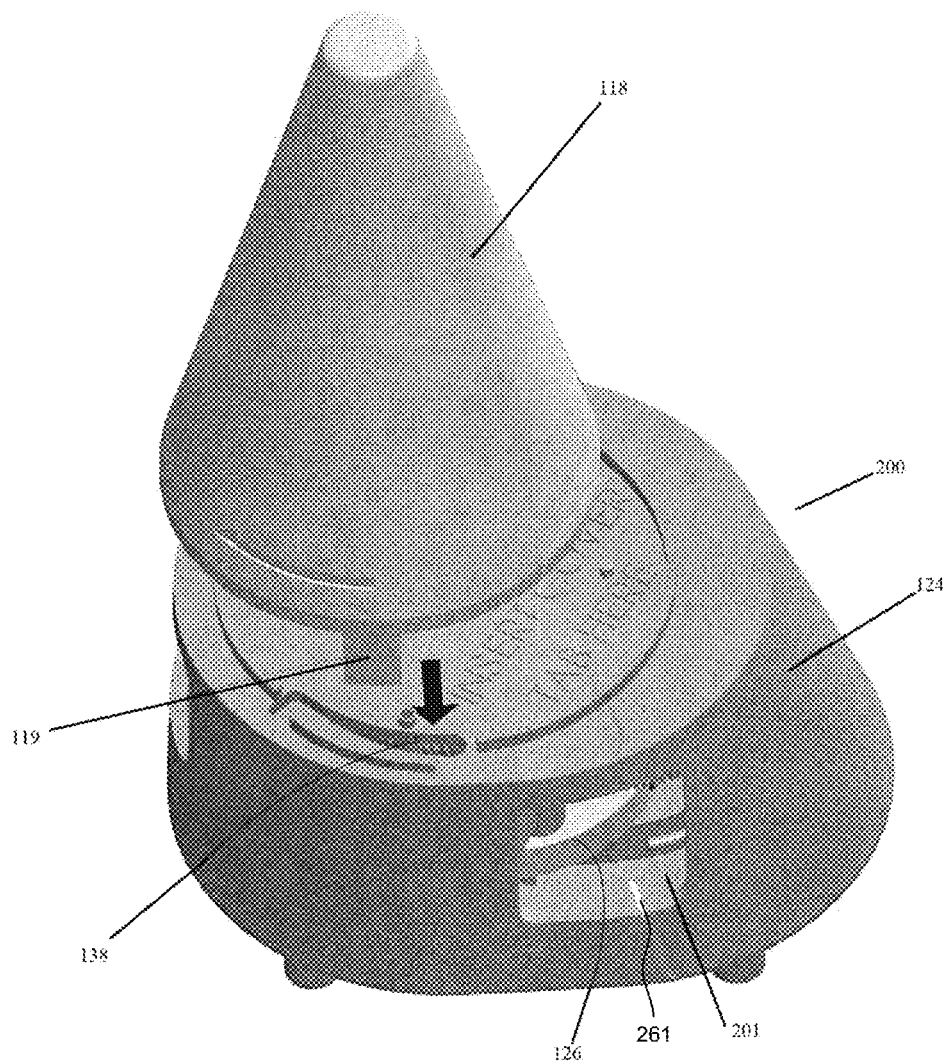
FIG. 17 is a top perspective view of the container cover above the powertrain base of the centrifuge of FIG. 1, in accordance with an aspect of the present invention.

Referring to FIG. 17, the protective cover 118 with a trigger tab 119 positioned over the powertrain base 200, having the powertrain cover 124, and the pawl 126 is depicted through first side opening 161 of the base holes 201. The protective cover 118 is positioned with the trigger tab 119 above the trigger slot 138.

Figure 18:
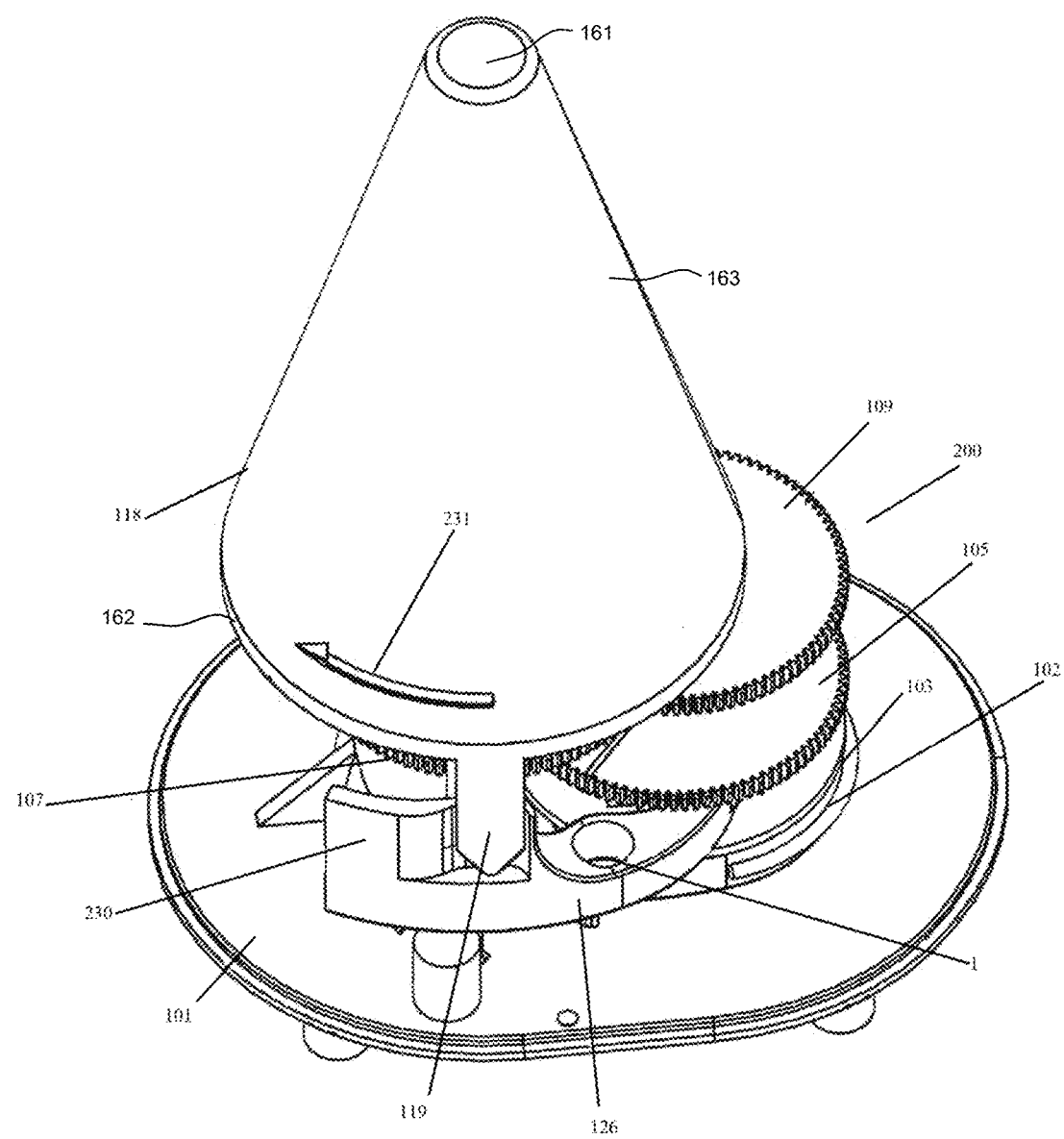
FIG. 18 is a top perspective view with the powertrain cover removed, of the container cover positioned to trigger the powertrain of the centrifuge of FIG. 1, in accordance with an aspect of the present invention.

Referring to FIG. 18, the internal mechanism of the powertrain base 200 is shown. The powertrain 120, with the pawl 126 positioned on the baseplate 101 with the protective cover 118 and the trigger tab 119 positioned, as if inserted into the trigger slot 138 (see FIG. 17) of the powertrain cover 124 (see FIG. 17). The protective cover 118 is shown with a top end 161 extending to a base end 162 with a circumferential sidewall 163 therebetween. The pawl 126 is shown in relation to powertrain 200 as if a pawl rocker slot 209 were positioned on the pawl support 153. An arrow 231 is depicted on the protective cover 118 to indicate the direction the protective cover 118 may be turned to activate the powertrain 120.

Figure 19:
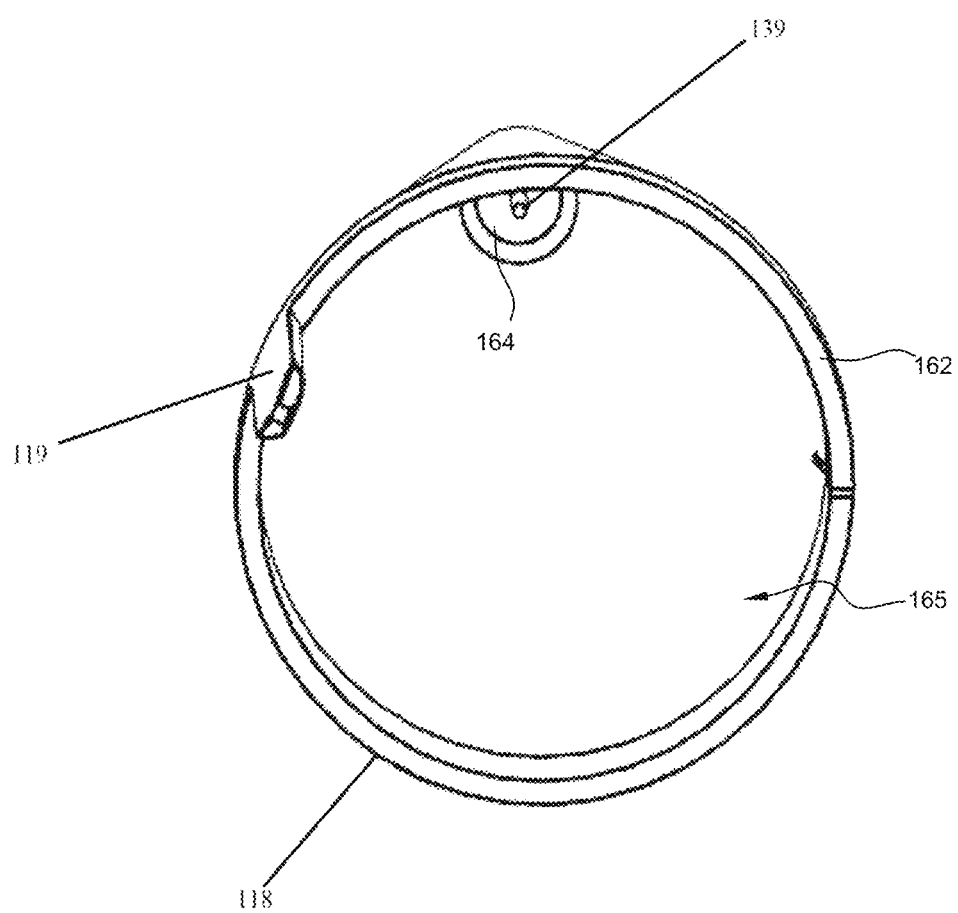
FIG. 19 is a bottom perspective view of the container cover of the centrifuge of FIG. 1, in accordance with an aspect of the present invention.

Referring to FIG. 19, the protective cover 118 is shown with the trigger tab 119, and the protective cover axle 139. The trigger tab 119 is shown extending away from the base 162. An opening 165 in the base 162 extends to the bottom side 164 of the top end 161. The protective cover axle 139 may, for example, extend out from the bottom side 164.

Figure 20:
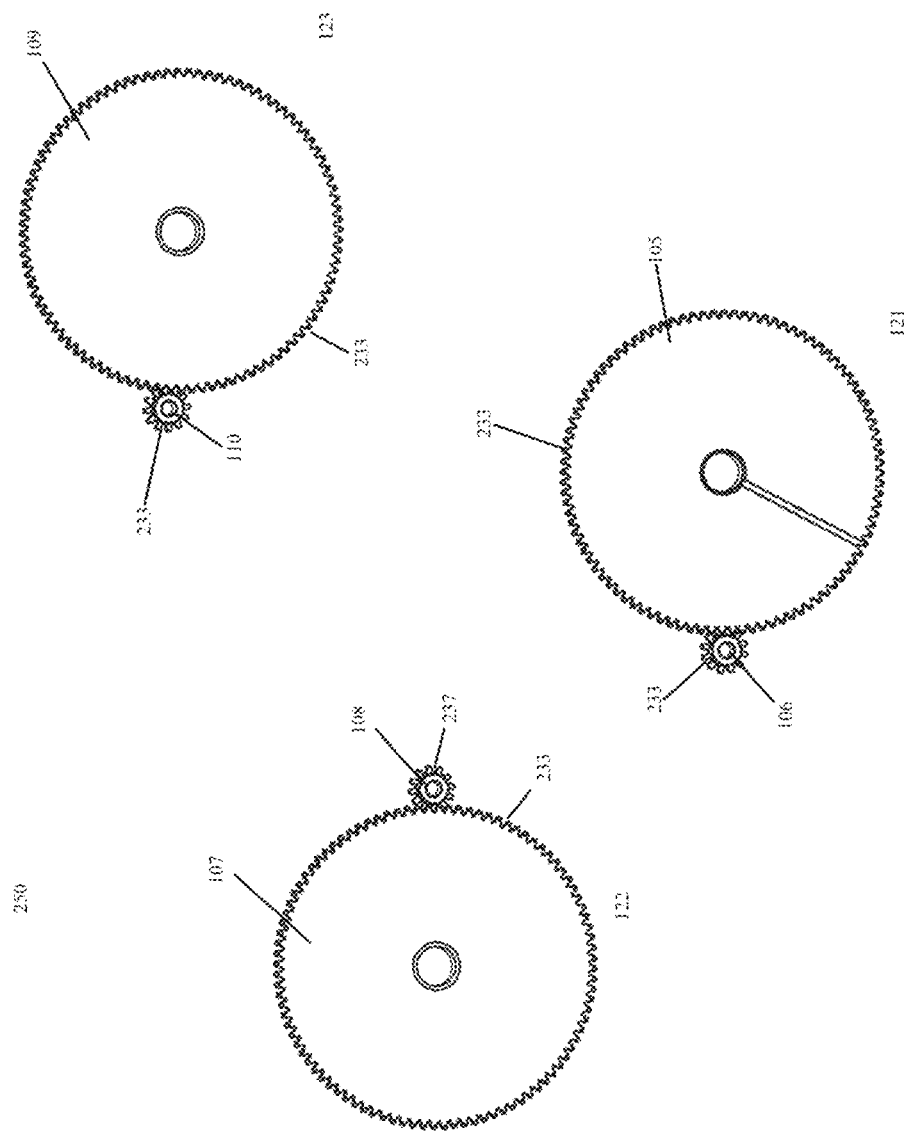
FIG. 20 is a top view of a plurality of powertrain gear pairs of the powertrain of FIG. 10, in accordance with an aspect of the present invention.
Figure 21:
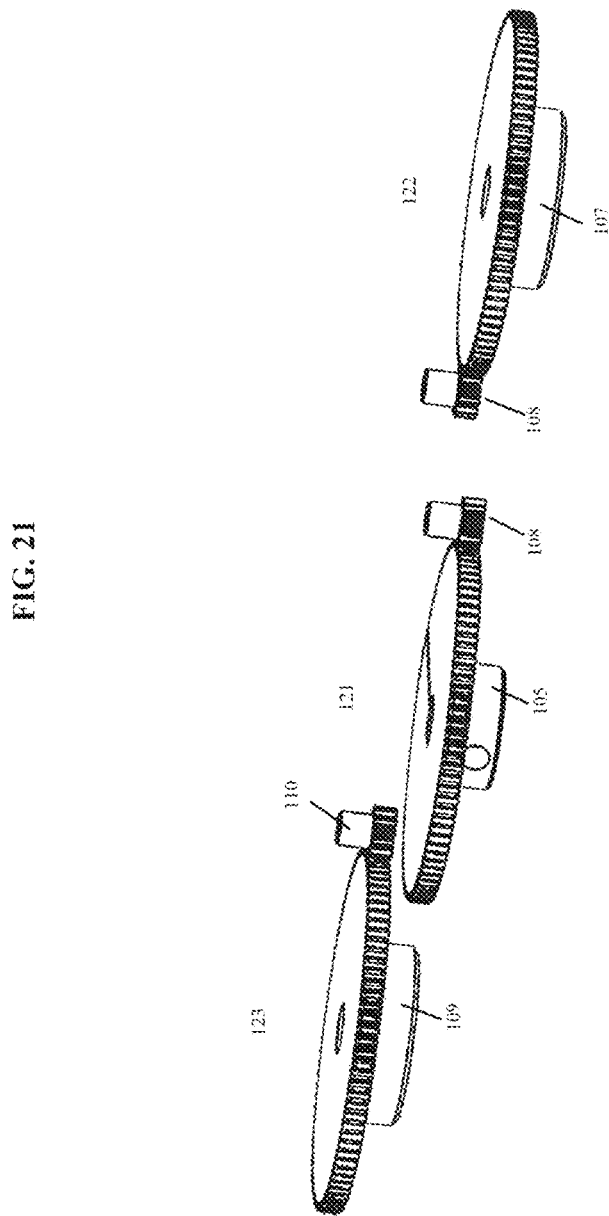
FIG. 21 is a perspective view of a plurality of powertrain gear pairs of FIG. 18, in accordance with an aspect of the present invention.

FIGS. 20 and 21, show a plurality of gear pairs 250 which may include, for example, the first gear pair 121, the second gear pair 122, and the third gear pair 123. The arrangement of gears is shown to identify an embodiment using three meshing pairs to increase rotational speed. The first gear pair 121 may have a first large gear 105 and a first small gear 106. The second gear pair 122 may have a second large gear 107 and a second small gear 108. The third gear pair 123 may have a third large gear and a third small gear.

Referring generally to FIGS. 4-21, powertrain 120 may, for example, be configured in a pair of assemblies, vertically positioned relative to the baseplate 101, to allow the plurality of gear pairs 250 to be enmeshed and to increase rotational speed from input into the first gear pair 121 to output at the third gear pair 123. The first assembly has the first large gear 105, the second small gear 108, and the third large gear 109. The second assembly has the first small gear 106, the second large gear 107, and the third small gear 110.

Referring to FIGS. 4-21, a method of assembling the first assembly of powertrain 120 may, for example, include placing the wind shaft 111 through baseplate connector hole 152, so wind shaft is maintained perpendicular to the baseplate 101. The baseplate wind shaft connector hole 152 may inhibit perpendicular or lateral movement of wind shaft 111 relative to the baseplate 101, but allow longitudinal axial rotational movement of the wind shaft 111 about the wind shaft longitudinal axis 210. The coil spring motor 102 may be threaded into the wind shaft 111 by placing the coil spring first end 237 into the coil spring connector 239. The coil spring second end 238 may be connected to baseplate 101 at the base ground post 157. The coil spring motor 102 may be wound around the wind shaft 111, and the coil spring motor 102 may be kept from unravelling by the coil spring restraint 236. Upon release, the coil spring motor 102 may cause the wind shaft 111 to rotate about the wind shaft longitudinal axis 210 within the baseplate wind shaft connector hole 152.

The coil spring washer 103 may be placed onto the wind shaft 111 above the coil spring motor 102, and the coil spring motor 102 may be positioned between the baseplate 101 and the coil spring washer 103. The coil spring restraint 236 may inhibit the coil spring motor 102 from unravelling radially from the wind shaft 111, and the coil spring washer 103 may inhibit the coil spring motor 102 from unravelling in a direction perpendicular to the baseplate 101. The coil spring washer 103 may be placed on the wind shaft 111 and allowed to rotate freely about the wind shaft 111.

The ratchet gear 104 may be connected to the first large gear 105 and placed onto wind shaft, with ratchet gear being directly above the coil spring washer 103. The first large gear 105 may be connected to the wind shaft 111, such that the first large gear 105 may be rotatably fixed with respect to the wind shaft 111. The ratchet gear 104 may also be connected to the wind shaft 111 or to the wind shaft 111 through the first large gear 105. An alternate embodiment may include the first large gear 105, and the ratchet gear 104 molded as a single unit. In this configuration, the wind shaft 111, the ratchet gear 104, and first large gear may be fixed with respect to each other but rotatable about the wind shaft longitudinal axis 210.

The first shaft 112 may be placed into the wind shaft aperture 240, with the first shaft 112 being collinear with the wind shaft 111 so that the first shaft 112 extends from the wind shaft aperture 240 in the distal direction from the baseplate 101, with the first shaft longitudinal axis 211, being substantially coaxial with the wind shaft longitudinal axis 210. The first shaft first end 221 may be in contact with the wind shaft 111. However, the first shaft 112 may be rotatable within the wind shaft aperture 240 relative to the wind shaft 111 or the first shaft 112 may be fixed at the first shaft second end 222, such that the wind shaft 111 rotates about the first shaft longitudinal axis 211, at the connection at the wind shaft aperture 240.

The second small gear 108 may be connected to the third large gear bushing 116 and the third large gear 109 may be connected to the third large gear bushing 116, such that the second small gear 108, the third large gear bushing 116, and the third large gear 109 are connected and rotatably fixed relative to each other. The combined the second small gear 108, the third large gear bushing 116 and the third large gear 109, may be placed onto the first shaft 112 to rotate about the first shaft 112, and the first shaft longitudinal axis 211. An alternate embodiment may include the second small gear 108 and the third large gear 109 molded as a single unit, placed onto first shaft 112 and rotatable about the first shaft longitudinal axis 211.

Further referring to FIGS. 4-21, a method of assembling the second assembly of powertrain 120 may, for example, include providing a second shaft 114 may have a second shaft first end 223 and a second shaft second end 224. The second shaft 114 may be placed into first base support 128 such that, for example, the second shaft 114 is perpendicular to the baseplate 101. The first small gear 106 may be connected to the first small gear bushing 113. The first small gear bushing 113 may be inserted into the second large gear bushing 115, with the second large gear bushing 115 being inserted into the second large gear 107. The combination of the first small gear 106, the first small gear bushing 113, the second large gear bushing 115, and the second large gear 107 may be placed onto the second shaft 114 such that the first small gear 106, the first small gear bushing 113, the second large gear bushing 115, and the second large gear 107 are connected and rotatably fixed relative to each other but rotatable about the second shaft 114. The first small gear 106 and the second large gear 107 may be molded as a complete unit and placed onto the second shaft 114 so as to be rotatably fixed relative to each other but rotatable about the second shaft 114. The first small gear 106 may be positioned such that the first large gear 105 and the first small gear 106 are enmeshed. The second large gear 107 may be positioned such that the second small gear 108 and the second large gear 107 are enmeshed.

As shown in FIGS. 4-21, assembling powertrain 120, may include positioning the first assembly on the baseplate 101 such that the wind shaft 111 and the first shaft 112 may be collinear to each other and perpendicular to the baseplate 101. The second assembly may be positioned on the baseplate 101, such that the second shaft 114 may be perpendicular to the baseplate 101. The first and second assemblies may be positioned so that the second shaft 114 and the combination of the wind shaft 111 and the first shaft 112 may be parallel and spaced relative to each other and to the baseplate 101, such that gears rotationally connected to the wind shaft 111 and the first shaft 112 may be enmeshed with gears rotationally connected to the second shaft 114.

FIGS. 5-16 show, the pawl 126 connected to a pawl roller 127, where the pawl 126 is connected to the pawl support 153 of the powertrain cover 124. The powertrain cover 124 may then be aligned with the baseplate 101, such that, for example, the first shaft second end 222 is aligned with and placed into the third shaft support 155 and the second shaft second end 224 is aligned with and placed through the second shaft support 129. First shaft 112 and second 114 may be fixed or rotatable within their respective supports. The powertrain cover 124 may be connected to the baseplate 101. The second shaft 114 may protrude through the second shaft support 129. The third small gear 110 may be connected to the container 117 at the container powertrain connector 151 such that the third small gear 110 is fixed with respect to the container 117. The third small gear connected to the container 117 may be placed onto the second shaft 114, such that the third small gear 110 is enmeshed with the third large gear 109. The third small gear 110 and the container 117 may rotate about second shaft 113 and about the second shaft longitudinal axis 223. The second shaft 114 may be rotationally free to move within the first shaft support 128, but the weight of the container 117 may be used to keep the second shaft 114 positioned within the first shaft support 128.

Figure 10:
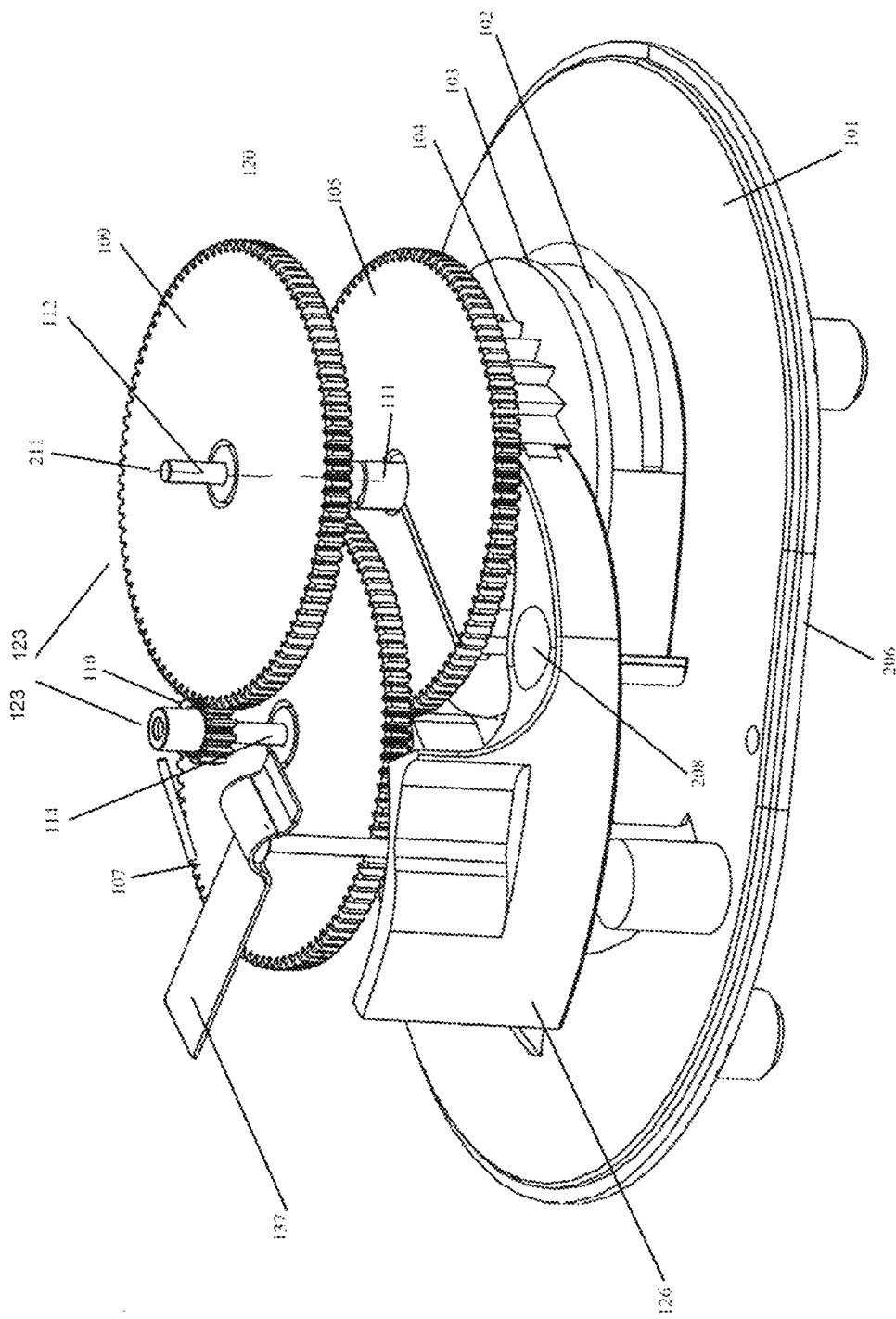
FIG. 10 is a perspective view of the powertrain of FIG. 9, in accordance with an aspect of the present invention.
Figure 11:
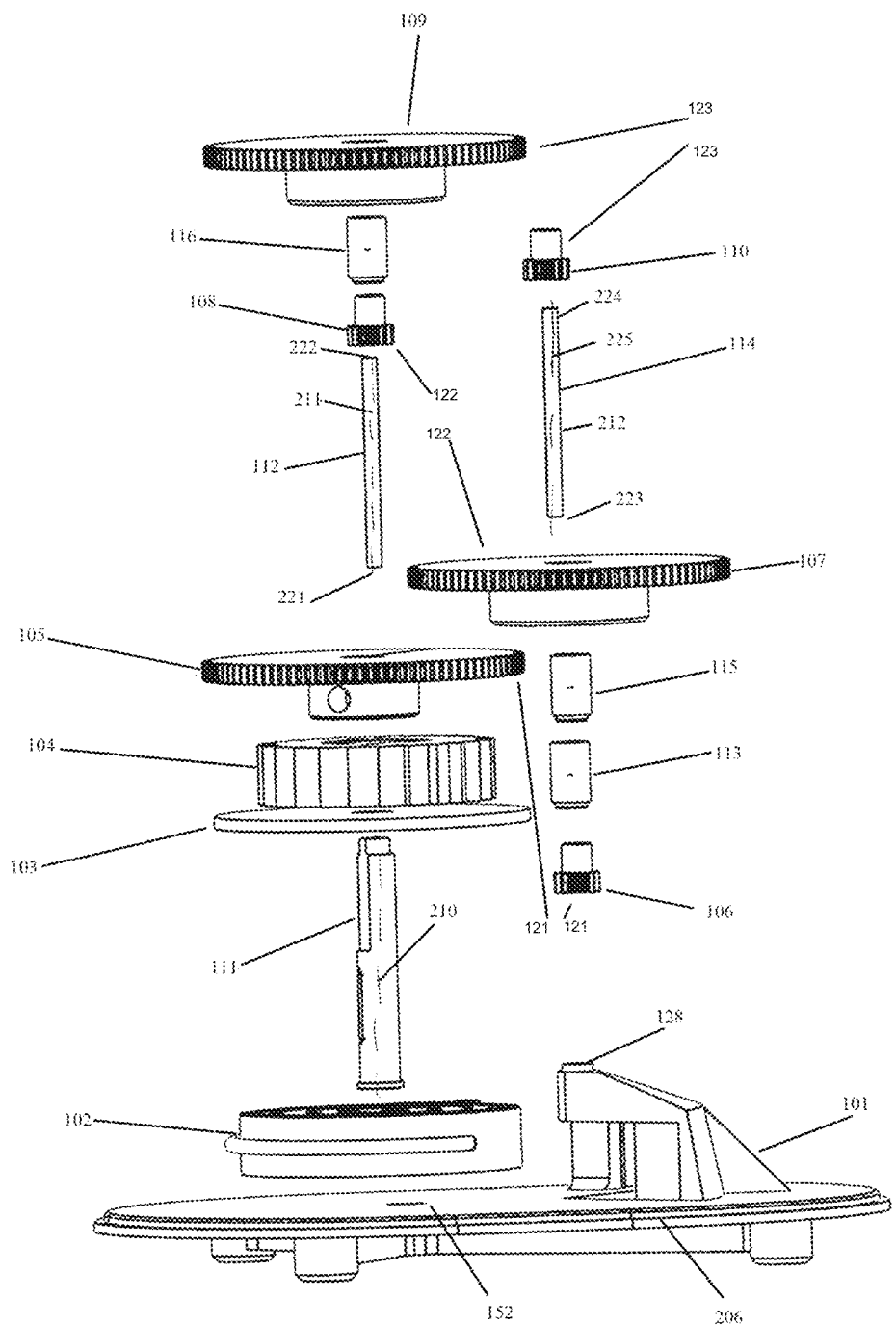
FIG. 11 is an exploded side view of the powertrain of FIG. 10, in accordance with an aspect of the present invention.
Figure 12:
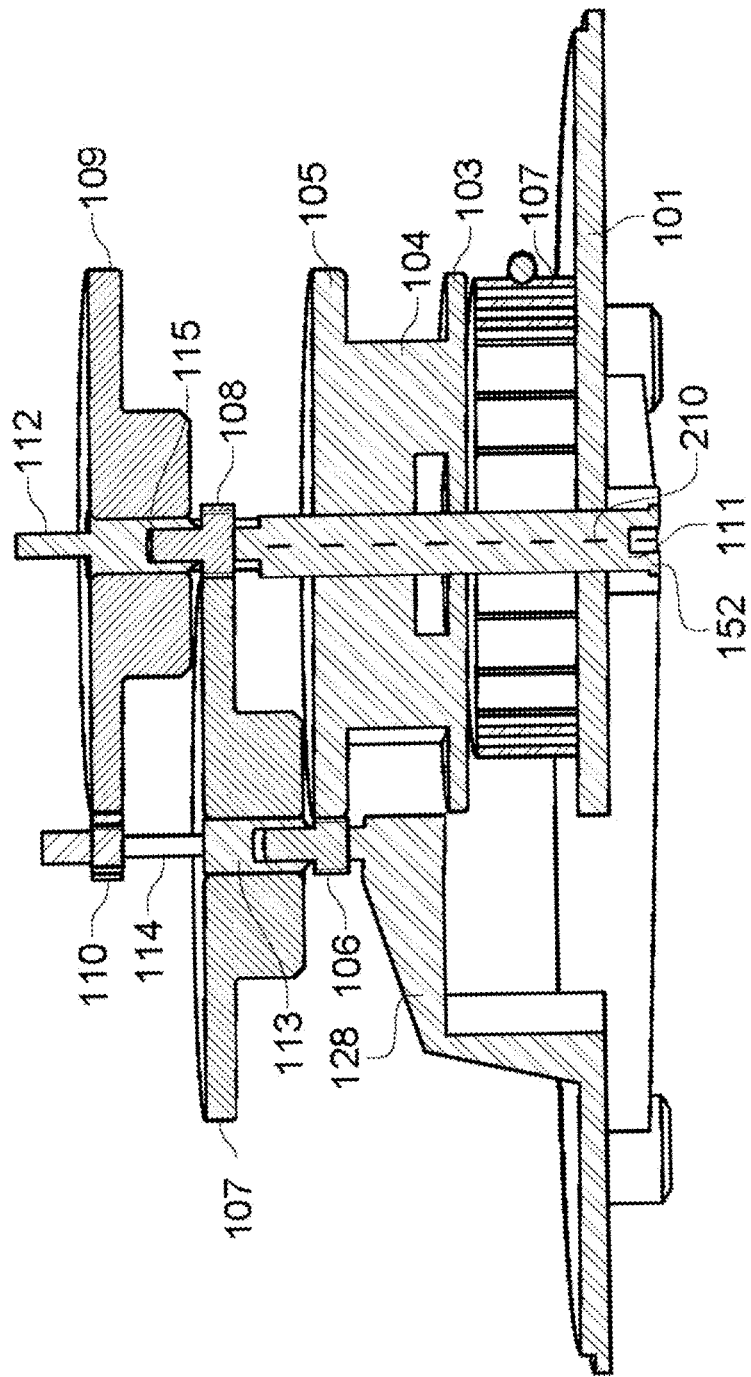
FIG. 12 is a cross sectional view of the powertrain of FIG. 10, in accordance with an aspect of the present invention.

As shown in FIG. 10, the coil spring motor 102 may be wound and the pawl 126 may be positioned such that the pawl roller 127 is in contact with the ratchet gear 104, preventing the coil spring motor 102 from unwinding or activating.

The centrifuge 100 assembly, as described, may provide desired rotational speed increases based on spring coil motor 102 torque on wind shaft 111, resulting in a desired rotational speed for container 117. In addition, the powertrain structure may also provide a compact and portable centrifuge. The current internal structure for centrifuge 100 may also provide for a single use or disposable device.

Referring to FIGS. 1-19, a method of use for centrifuge 100 includes the steps of removing the travel tape 135, removing the protective cover 118, removing the travel pin 137, inserting blood into the container 117, and replacing the protective cover 118 over the container 117 and onto the powertrain base 200, about the protective cover track 143, so that the trigger tab 119 is inserted into the trigger slot 138. Further, twisting the protective cover 118 in the direction of the arrow 231, rotates the trigger tab 119 and moves the pawl 126 away from the ratchet gear 104, releasing soil spring 102, and thereby activating the powertrain 120 to spin the container 117. The container 117 may continue to spin until all momentum of the powertrain 120 and the container 117 dissipates.

As shown in FIGS. 1-19, by placing the protective cover 118 onto the powertrain base 200 and inserting the trigger tab 119 into the trigger slot 138, and twisting the protective cover 118 in the direction of arrow 131, the trigger tab 119 may activate powertrain 200 by pushing the end of the pawl 126 distal to pawl roller 128, such that the pawl 126 pivots about the pawl powertrain base connector 208 connected at the pawl rocker slot 209. The pawl 126 may pivot such that the pawl 126 end connected to pawl roller 128 and in contact with the ratchet gear 104, is moved away from the ratchet gear 104, allowing the ratchet gear 104 to move freely. Coil spring motor 102, may be wound and assembled to a desired tension and may be made from a material to impart a desired torque onto the wind shaft 111.

With the ratchet gear 104 allowed to move freely, without the pawl 126 inhibiting rotation, the coil spring motor 102 is released and may impart torque on the wind shaft 111, thereby rotating the wind shaft 111. The wind shaft 111, being connected to the coil spring washer 103 and the first large gear 105, and with first gear 105 connected to ratchet gear 104, may cause the first large gear 105 to rotate about the wind shaft longitudinal axis 210 as the coil spring motor 102 is released. The first large gear 105, enmeshed with the first small gear 106, may cause the first small gear 106 to rotate about the second shaft 114 and the second shaft longitudinal axis 225. The first small gear 106 being connected to the second large gear 107 by the first small gear bushing 113 and the second large gear bushing 115, may cause the second large gear 107 to rotate about the second shaft 114 and the second shaft longitudinal axis 225. The second large gear 107 may be enmeshed with the second small gear 108, causing the second small gear 108 to rotate about the first shaft 112 and the first shaft longitudinal axis 211. The second small gear 108, being connected to the third large gear 109 by third large gear busing 116, may cause the third large gear 109 to rotate about the first shaft 112 and the first shaft longitudinal axis 211. The third large gear 109, being enmeshed with the third small gear 110, may cause the third small gear 110 to rotate about the second shaft 114 and the second shaft longitudinal axis 225. The third small gear 110, being connected to the container 117 at the container powertrain connector 151, may cause the container 117 to rotate about the second shaft 114 and the second shaft longitudinal axis 225.

The protective cover 118 may have the protective cover axle 139 which can be inserted into the stopper opening 232 when the protective cover 118 is placed over the container 117 and onto the powertrain base 200. The protective cover axle 139 may allow the container 117 to have support at the container powertrain connector 151 and at the stopper opening 232 about the protective cover axle 139. Support at two ends of the container 117 may keep the container 117 balanced and rotating about an extension of the second shaft longitudinal axis 225 towards the protective cover axle 139. The protective cover axle 139 may be used to provide balance for the centrifugal container 117 when rotating.

An alternate embodiment may have a sealed bearing at the container powertrain connector 151 where the container 117 passes through the container base opening 205, to aid in providing balance. The container 117 may have rotational balance without either an axle or a bearing.

The process of separating the blood 180 to obtain PRP may be achieved, for example, by removing the protective cover 118, inserting blood into the container 117, placing the protective cover 118 over the container 117 and the trigger tab 119 into the trigger slot 138, and twisting the protective cover 118 in the direction of the arrow 231 thereby activating the powertrain 120 and rotating the container 117. Once the container 117 has stopped spinning, the blood 180 may have separated into three layers, with the platelet poor plasma 181 being on top, the PRP 182 in the middle, and red blood cells 183 on the bottom of the container 117. For example, placing 30 ml-50 ml of blood into centrifuge 100, the PRP volume recovered may be approximately 5-7 ml.

While the trigger tab 119 is connected to the protective cover 118, it may be used to pivot the pawl 126 away from the ratchet gear 104, an alternate embodiment may be, for example, a button, switch, lever, or other release mechanism sufficient to release the ratchet gear 104 and activate the coil spring motor 102.

Referring to FIGS. 9-15, 20 and 21, centrifuge 100 may have a powertrain 120 with the plurality of gear pairs 250 equal to three. To rotate three gear pairs 250, the coil spring motor 102 may, for example, impart approximately 5-10 in-lbs. of torque onto the wind shaft 111, resulting in 6-10 rpm of rotational speed. A higher or lower torque spring coil motor 102 may be used to provide the desired the rotational input speed of the wind shaft 111. With a first gear pair 121, the second gear pair 122, and a third gear pair 123 having gear ratios of, for example, 8:1, and initial wind shaft rotation speeds of 6-10 rpm may result in the container 117 rotation at approximately 3072-5120 rpm. First gear pair 122 rotation speeds may, for example, range from approximately 48-80 rpm. The second gear pair 122 rotation speeds may, for example, range from approximately 384-640 rpm. The third gear pair 123 rotation speeds may, for example, range from approximately 3072-5120 rpm. With the container 117 connected to the third small gear 110, the container 117 may rotate at approximately the speed of the third small gear 110 (e.g. 3072-5120 rpm). The plurality of gear pairs 250 may have the gear teeth 233. The first large gear 105, the second large gear 107, and third large gear may each have, for example, ninety-six teeth 233. The first small gear 106, the second small gear 108, and the third small gear 110 may each have, for example, twelve teeth. Small gears may have, for example, from ten to fifteen teeth, and large gears may have from eighty to one-hundred and twenty teeth, respectively for gear ratios of 8:1. This gear sizing may accommodate a powertrain structure which would fit into an enclosure sized for spaces available on a sterile surgical table. Gear ratios may also vary, ranging from, for example, 6:1-12:1. This sizing also may accommodate portability and use in locations where centrifuges requiring an electrical outlet for power may not be used.

Still referring to FIGS. 9-15, 20 and 21, three gear pairs are depicted with each pair having gear rations of 8:1. There may be embodiments with, for example, more gear pairs or fewer gear pairs. There may also be embodiments with, for example, different gear ratios. Blood separation in a centrifugation process generally occurs when rotated at speeds at or above 3000 rpm, a combination of gear pairs and ratios that raise the rotational speed of the container 117 to at or above 3000 rpm may be used. Shaft lengths, the number of bushings, and torque output of the coil spring motor 102 may need to be adjusted accordingly. The gears shown in the embodiments may be spur gears, however other gear types, for example, helical, worm, beveled, or planetary gear types may be used. Rather than the plurality of gear pairs 250, an alternate embodiment may have gears in meshed formations other than pairs.

The coil spring motor 102, shown in FIG. 14, may impart full torque once released resulting in the container 117 experiencing a substantially immediate rotational acceleration from stopped to full or near full rotational speed, followed by a gradual slowdown, in a process known as differential centrifugation. A slowdown to stop period may be over a period of 1-3 minutes as the powertrain 120 and the container 117 gradually lose momentum.

In place of the plurality of gear pairs 250, the powertrain 120 may also use a plurality of, for example, belt and pulley pairs. For three belted pulley pairs, pulley sizing ratios within a pulley pair (not shown) may be 8:1, with belt tension being such as to approximate gear meshing. For such a configuration, the pulleys need not be in pairs, with the gear ratios and the pulley sizing varying to accommodate an imparted torque of 5-10 in-lbs. onto the wind shaft 111, resulting in 6-10 rpm of rotational speed. The pulleys and belts may be configured to increase rotational speeds, such that the container 117 may rotate at above 3000 rpm. The powertrain 120 may similarly use, for example, a chain and sprocket gear configuration.

Figure 13:
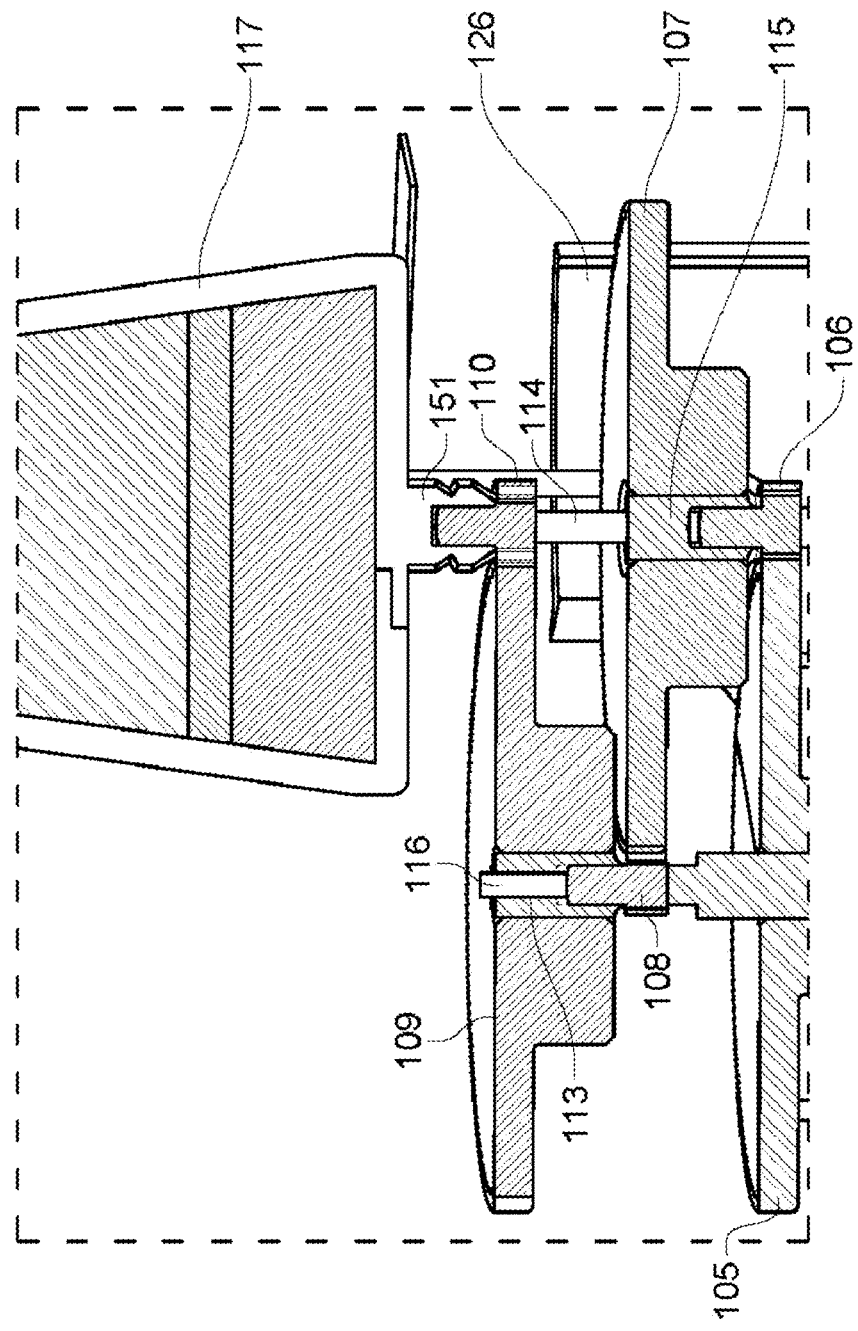
FIG. 13 is a cross sectional closeup view of a centrifugal container connection to the powertrain of FIG. 9, in accordance with an aspect of the present invention.

The coil spring motor 102, as shown in FIG. 13, is one embodiment of a power source, however other spring configurations, spring variants, and other mechanical stored energy sources may be used for the centrifuge motor. For example, rather than a spring, a hand crank with a tachometer for measuring container rotational speed may be used.

The plurality of gear pairs 250, shown in FIGS. 20-21, may be made from plastic (e.g. polyvinyl chloride, high-density polyethylene, polycarbonate, polypropylene, acrylonitrile butadiene styrene (ABS), or Teflon). The wind shaft 111, the first shaft 112, the second shaft 114, and the coil spring motor 102, shown in FIG. 11, may be made from a metal material (e.g. spring steel, stainless steel, or titanium). However, any suitable material for use in a medical environment may be used for any component of centrifuge 100. Gear materials that have lower friction, such as, for example, polypropylene or Teflon may be suitable gear materials.

Figure 22:
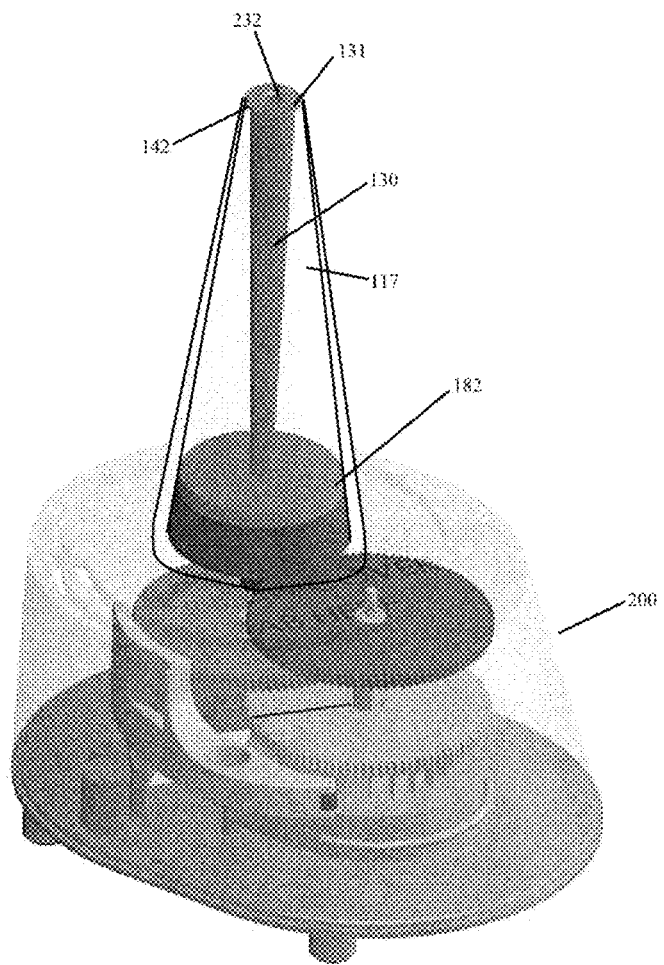
FIG. 22 is a top perspective view of the centrifuge of claim 3, with a siphon, in accordance with an aspect of the present invention.
Figure 23:
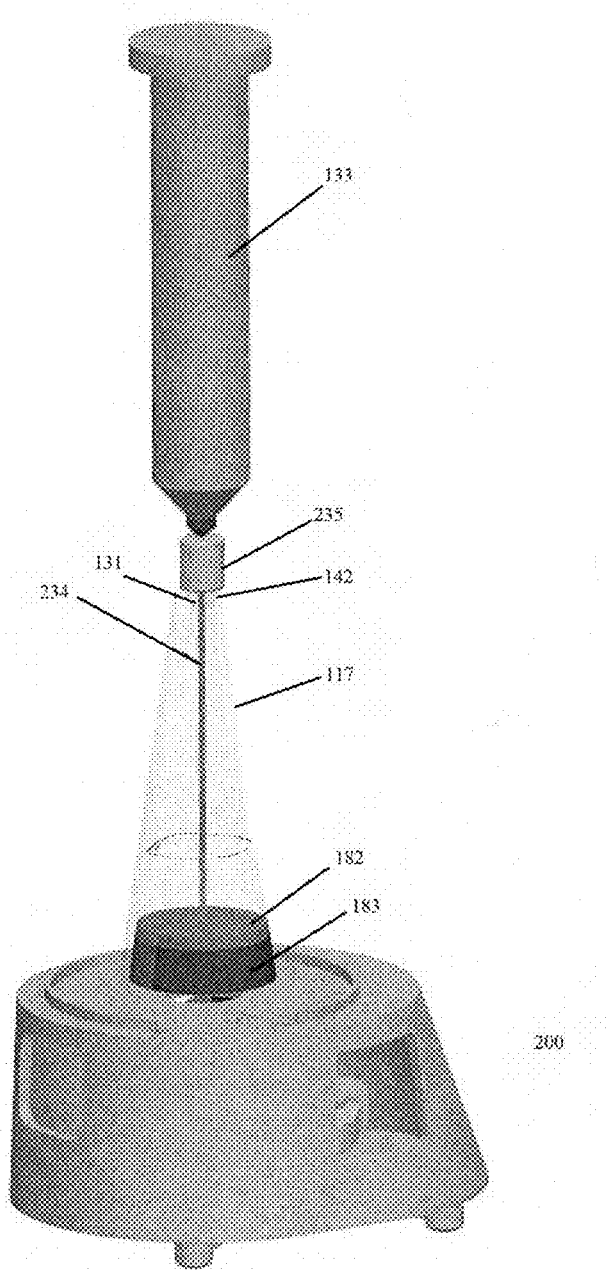
FIG. 23 is a perspective view of a syringe inserted into the container of FIG. 3, in accordance with an aspect of the present invention.

Referring to FIGS. 22 and 23, the powertrain base 200 may have a container 117 with, for example, the stopper 131 inserted into the container top opening 142, connected to a siphon 130 positioned at the level of the PRP 182. By inserting a syringe 133 and cannula 234 into the stopper opening 232, PRP may be extracted, through the siphon 130. In an embodiment without siphon 130, a spacer 235, may be mated with the stopper 131. A syringe 133 with a cannula 234 may be used to extract the PRP 182, where the cannula 234 is inserted through the spacer 235 and through the stopper 131 to the position of the PRP 182. The syringe may then be used to extract the PRP 182 and the cannula 234 withdrawn.

Figure 24:
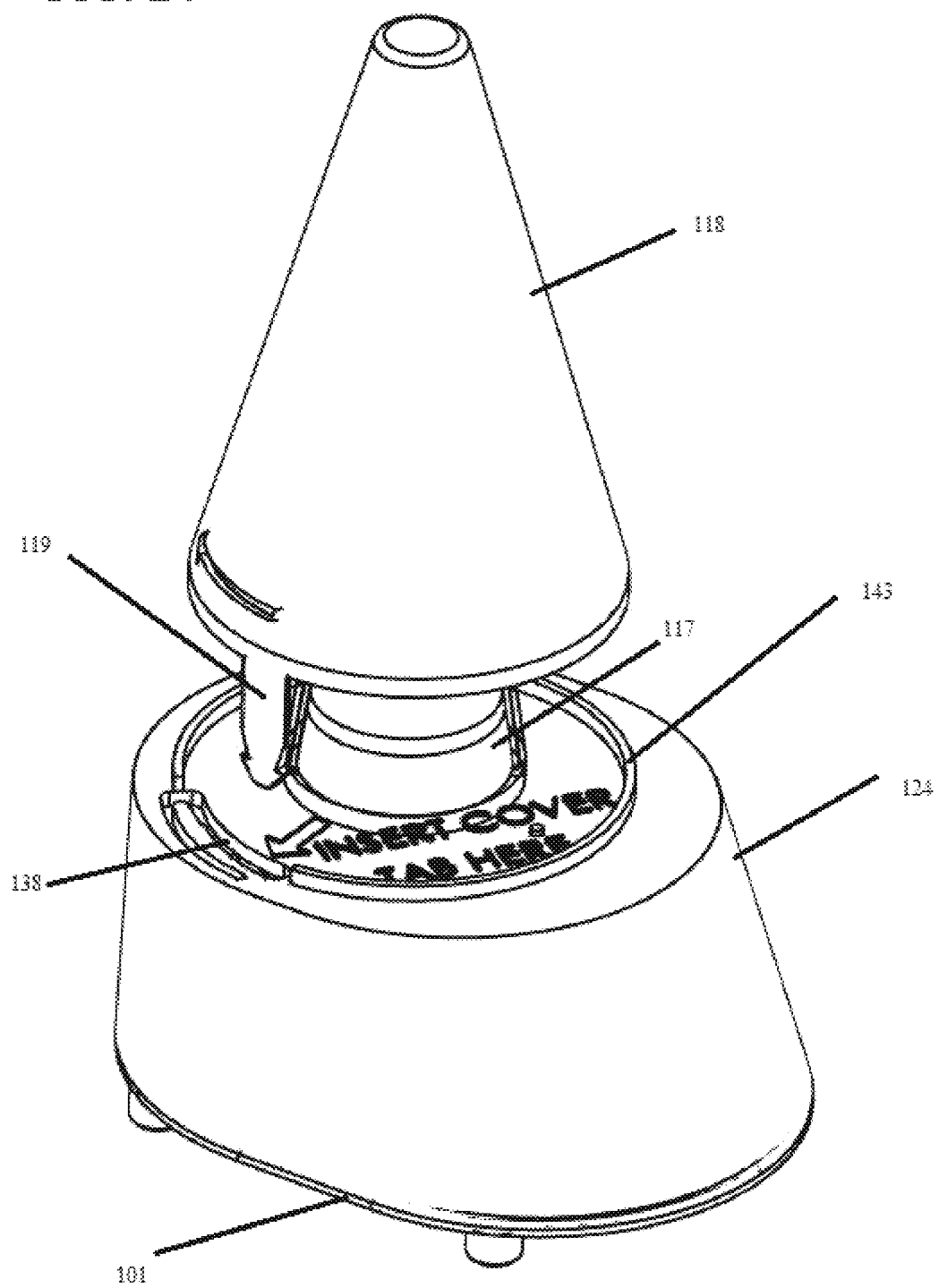
FIG. 24 is a perspective view of the centrifuge of FIG. 1, with a sealed powertrain cover, in accordance with an aspect of the present invention.
Figure 25:
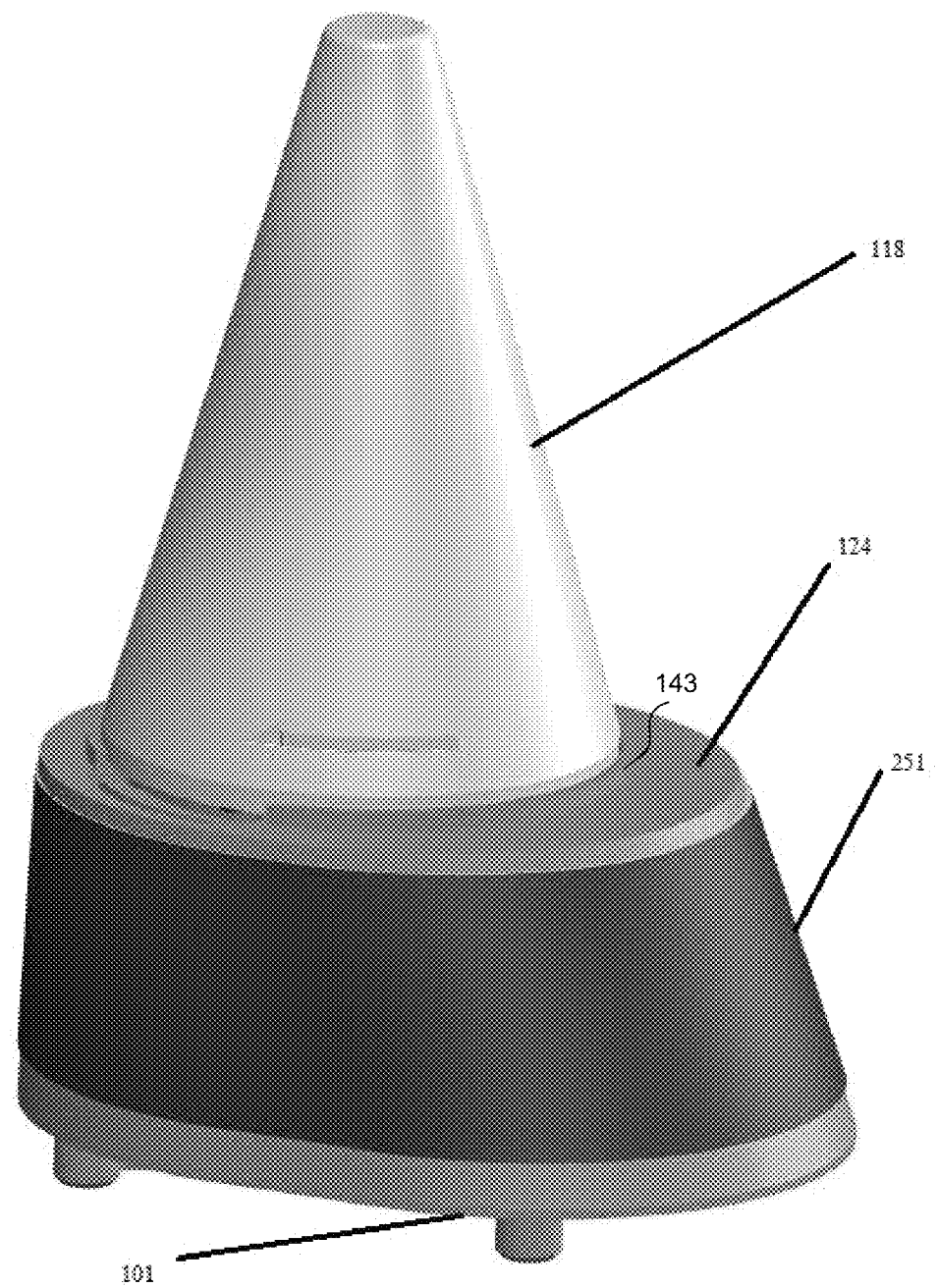
FIG. 25 is a perspective view of the centrifuge of FIG. 1, with the sealed powertrain cover, in accordance with an aspect of the present invention.

FIGS. 24 and 25 depict two embodiments with a sealed powertrain cover. In FIG. 24, the powertrain cover 124 is shown as a single monolithic piece with no base holes. In FIG. 25, a powertrain seal 251 is affixed to the powertrain cover 124. The powertrain seal 251 may include material such as tape, rubber, plastic, or shrink-wrap. Any the base holes 201 may be covered by the powertrain seal 251 after the powertrain is wound and sterilized.

Figure 26:
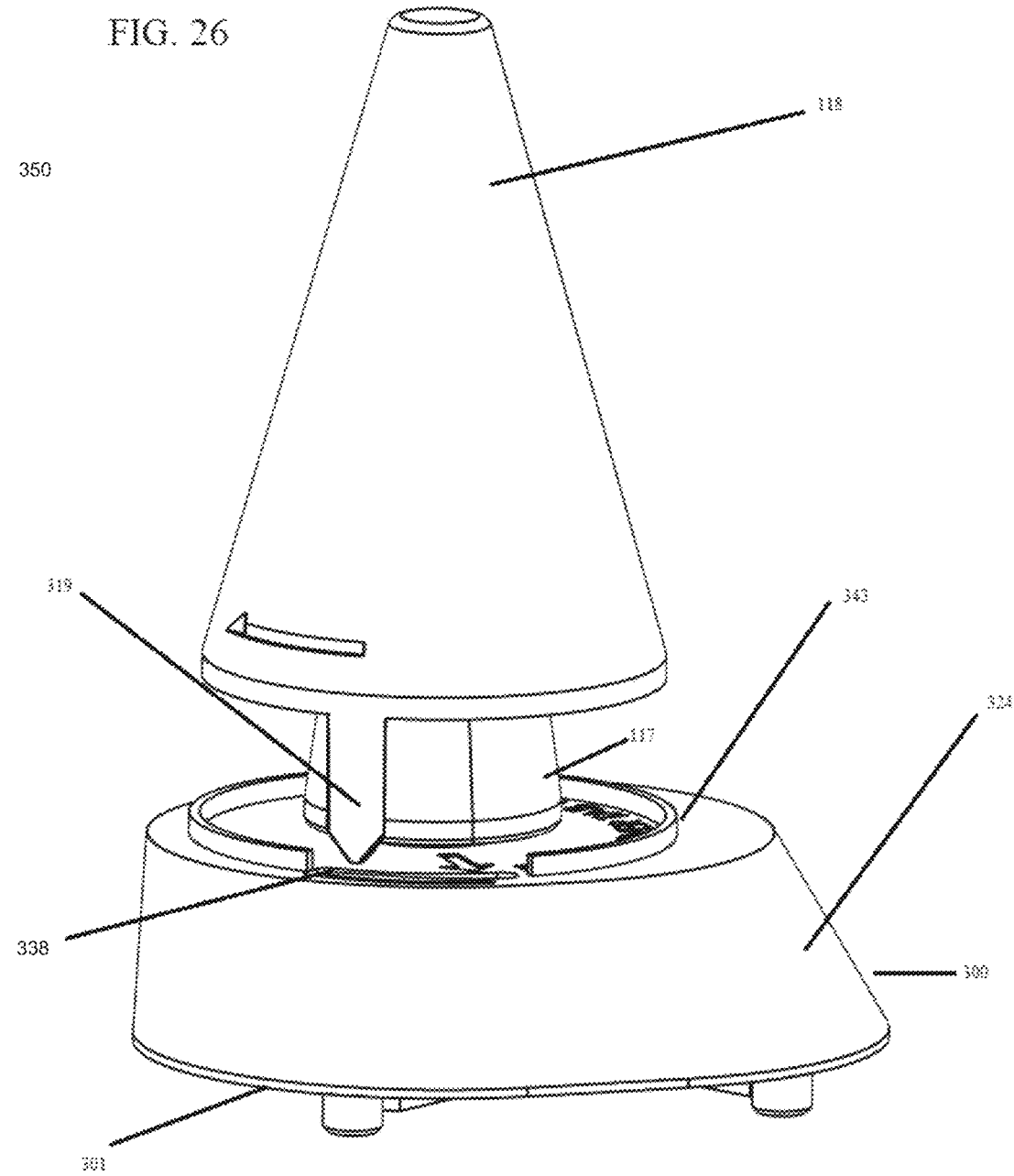
FIG. 26 is a perspective view of the centrifuge of FIG. 1, showing a DC motor powertrain, in accordance with an aspect of the present invention.
Figure 28:
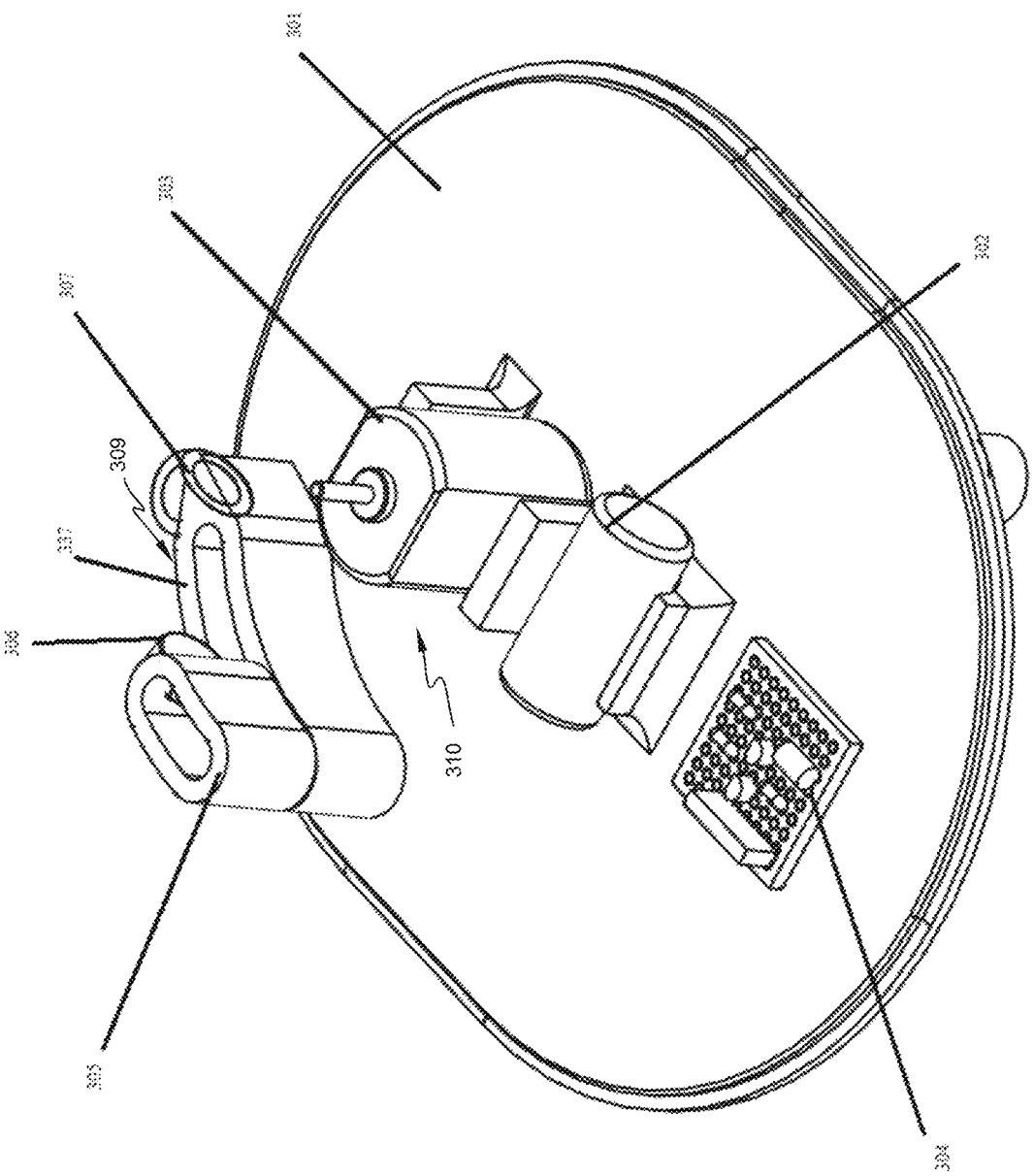
FIG. 28 is a perspective view of another embodiment of the powertrain of the centrifuge of FIG. 26, in accordance with an aspect of the present invention.
Figure 29:
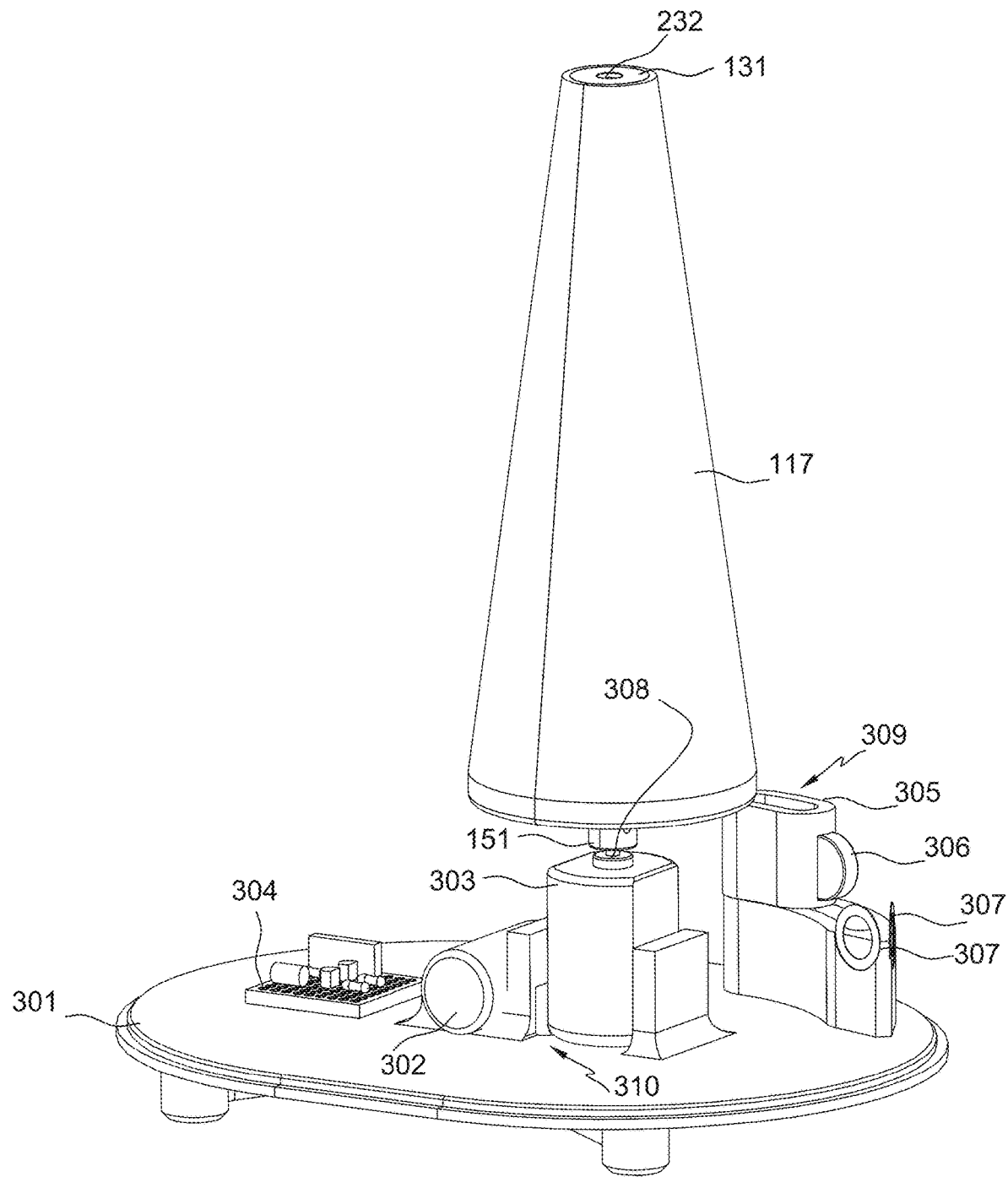
FIG. 29 is a side view of the powertrain and container of the centrifuge of FIG. 26, in accordance with an aspect of the present invention.

FIGS. 26-29 show, in another embodiment, a centrifuge 350 with an electrical rotational mechanism 310 contained within an electrical powertrain base 300. Referring to FIG. 26, the electrical powertrain base 300 is shown having a powertrain cover 324, an electrical baseplate 301, a protective cover track 343, and a trigger slot 338. The protective cover 118 is shown with a trigger tab 319, positioned above the trigger slot 338. The container 117 may be, for example, the same as described above for centrifuge 100.

Referring to FIGS. 4, and 27-29, the interior of the electrical powertrain base 300 is shown. The powertrain cover 324 has a container top opening 342, the trigger slot 338, and the cover track 343. The protective cover 118 may, for example, be seated within the protective cover track 343 shown in FIG. 26, similar to the protective cover 118 seated within protective cover track 143 as shown in FIG. 2. In FIG. 27, affixed to the electrical baseplate 301 are an electrical motor 303, an internal electrical power source 302, and a printed circuit board 304. A rotor shaft 308 extends from the electrical motor 303. More specifically, the electrical motor 303 may be, for example, a direct current (DC) motor. The internal electrical power source 302 may be, for example, a chemical battery, a solid state battery, or a capacitor with stored charge. Also shown is a switch 309 having a switch slider 305, a magnet 306, a trigger track 337, and metal shims 307. The magnet 306 may be, for example, positioned on a side of the switch slider 305 facing the metal shim 307. The switch 309 may have, for example the switch slider 305 at a first end of the trigger track 337 and the metal shims 307 at a second end of the trigger track 337. Conductive wires (not shown) may connect the DC motor 303, the electrical power source 302, the printed circuit board 304, the switch slider 305, the magnet 306, and the trigger track 337. Conductive wires (not shown) may be within the electrical baseplate 301. The rotational mechanism 310 may, for example, have a circuit including the electrical motor 303, the switch 309, the internal electrical power source 302, and/or the circuit board 304. The container 117 may be inserted into the container top opening 342 (see FIG. 27), so that the container powertrain connector 151 (see FIG. 29) connects to the rotor shaft 308 (see FIG. 29), in a direct drive configuration. The rotor shaft 308 may have a rotor longitudinal axis (not shown) and be connected to the container 117, such that the rotor shaft 208 and the container 117 both rotatably move about the rotor longitudinal axis.

Further referring to FIGS. 26-29, the electrical motor 303, may for example, rotate the container 117 at speeds from 0 rpm to approximately 20,000 rpm and may provide for sustained user control during the centrifugation process to ensure that blood separation occurs. By inserting the trigger tab 319 into the trigger slot 338, the trigger tab 319 may extend into the switch slider 305. The trigger tab 319 may be, for example, fabricated from a conductive metal, connecting the magnet 306 on the switch slider 305 with the trigger tab 319. In another example of the present invention, the trigger tab 319 may be fabricated from a polymer or non-conductive material. The protective cover 118 may have a longitudinal axis (not shown) extending from the top end 161 along the axle 139. By rotating the protective cover 118 about the longitudinal axis, the trigger tab 319, may pull the switch slider 305 along the trigger track 337, to connect the magnet 306 along the side of the switch slider 305 to shims 307. By contacting the shims 307 and by being connected to the switch slider 305, a circuit may be completed between the electrical motor 303, the power source 302, and the circuit board 304. Thus, the power source 302 powers the motor 303. Circuit board 304 may include a timer (not shown) to control how long power from power source 302 continues to the electrical motor 303. In other embodiments, the power output and rotational speed of the electrical motor 303 may be controlled by, for example, using trigger tab to adjust the voltage of the power source 302 to the electrical motor 303, and thereby controlling rotational speed of the container 117.

Further referring to FIGS. 4, 19, and 26-29, the internal electrical power source 302 and the electrical motor 303 may be sealed and sterilized or completely enclosed within the electrical powertrain base 300, such that the container 117 may protrude from the container top opening 342, and be rotated through a sealed connection with the DC motor 303. The connection to the electrical motor 303 may be through a sealed bearing (not shown) connected to the container top opening 342. The protective cover 118 may still have the protective cover axle 139, which may be inserted into the stopper opening 232 to provide a second support about which the container 117 may rotate.

In still other embodiments, centrifuge 350, may utilize the electrical motor 303, with varying gears and shafts (not shown), for example, to adjust the speed of the container 117. The presence of gears may depend on the power output of the motor and torque requirements for rotating the container 117. In another embodiment, the electrical motor 303 may have, for example, a direct drive configuration where a motor shaft is directly connected to the container 117. The direct drive configuration may, for example, limit or even negate the use of bearings or bushings It is also possible that a hybrid system having a mechanical motor and a DC electrical motor may be used.

The centrifuge 100 may also use mechanically stored energy (e.g. coil spring motor 102) to power the mechanical powertrain 120 or a battery to power the electrical rotational mechanism 310, to spin the container 117 to speeds from 3000 to 20,000 rpm. The container 117 may be supported by the powertrain 120 or the electrical rotational mechanism 310 at a first end and the protective cover axle 139 at a second end. The spin of the container 117 may be stopped by the depletion of energy or by a timer (not shown).

Figure 30:
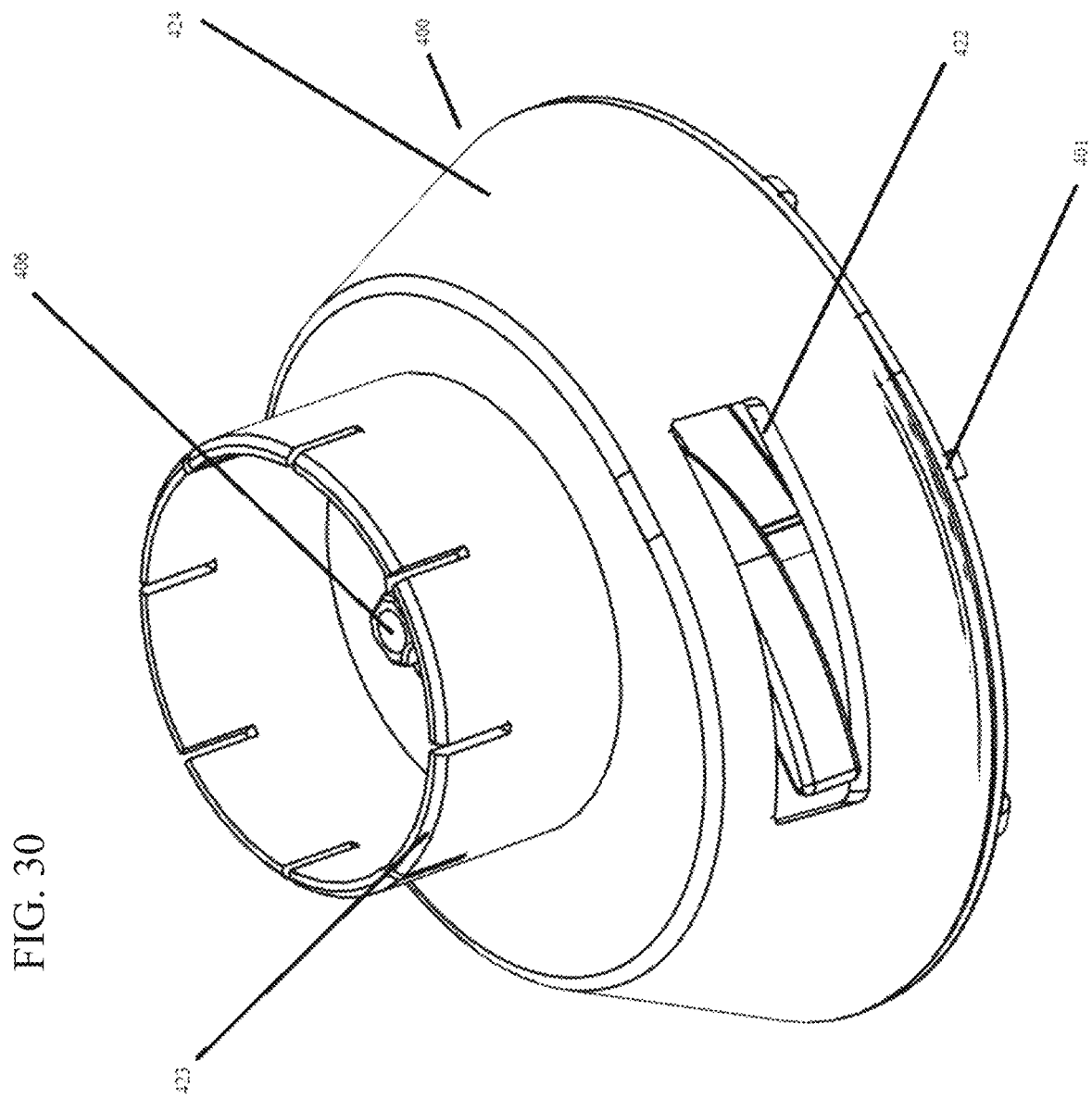
FIG. 30 is a perspective view of a powertrain base of a bone cement mixer centrifuge, in accordance with an aspect of the present invention.

Referring to FIG. 30, a mixer powertrain base 400 for a bone cement mixer is shown, having a mixer baseplate 401, a mixer powertrain cover 424, a mixer base hole, a collar 423, and a paddle drive shaft 406.

Figure 31:
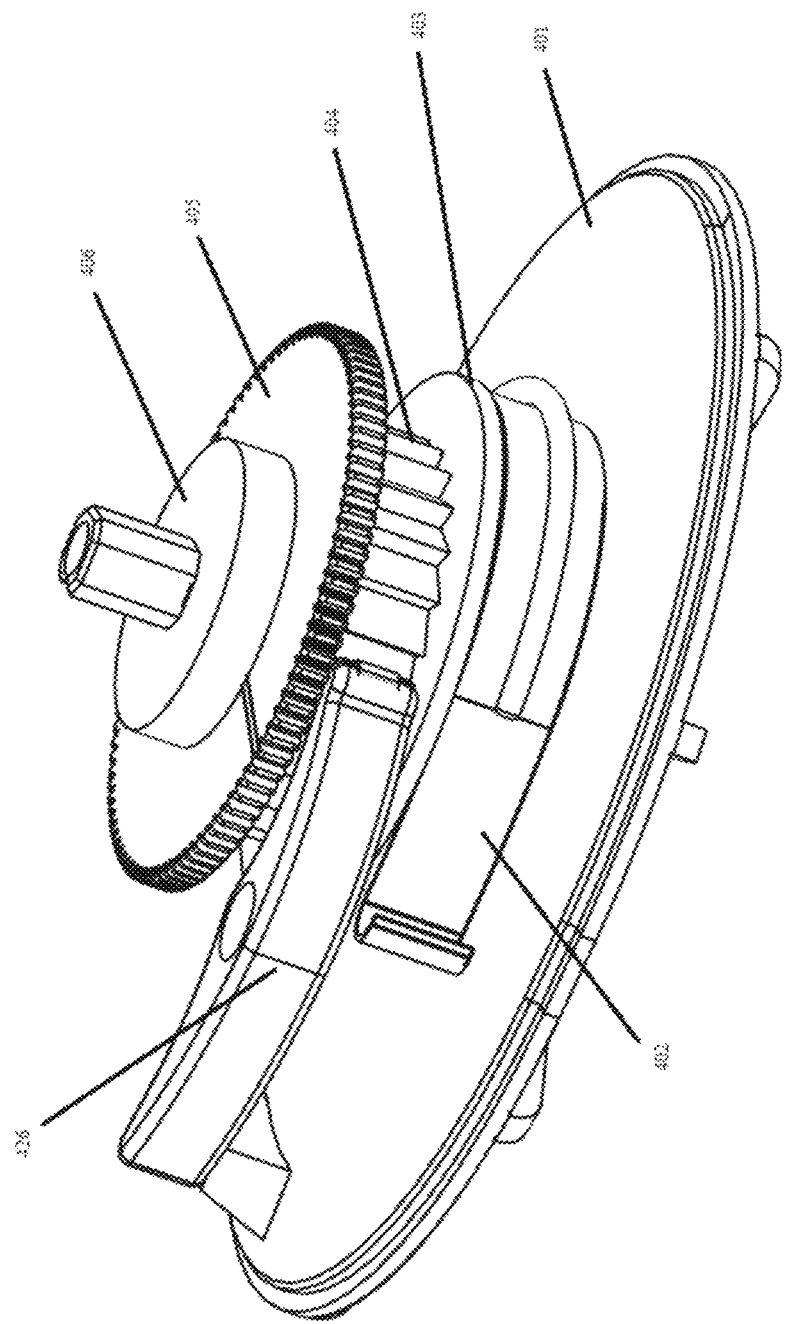
FIG. 31 is a perspective view of the powertrain of the bone cement mixer centrifuge of FIG. 29, in accordance with an aspect of the present invention.
Figure 32:
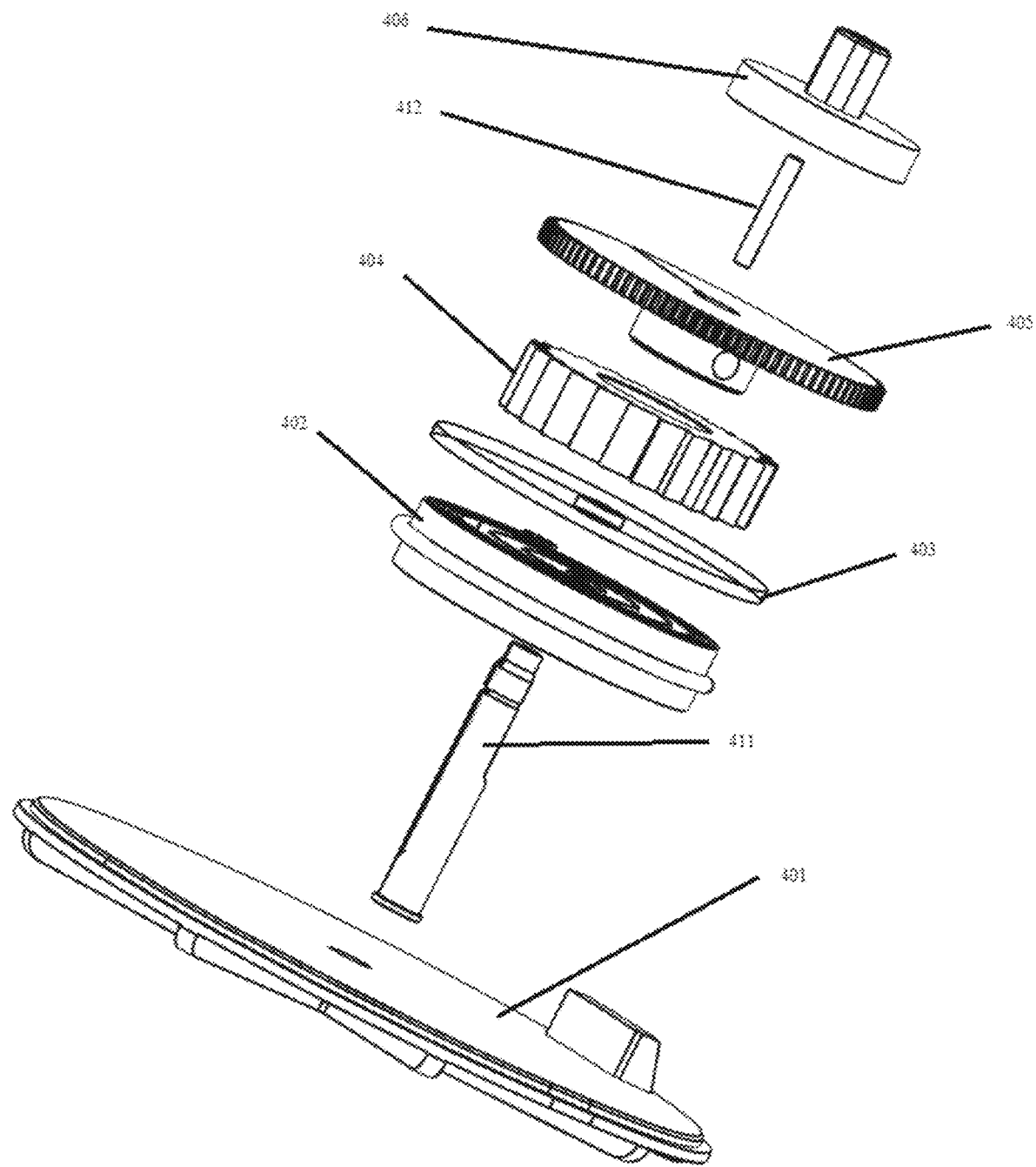
FIG. 32 is an exploded view of the powertrain of the bone cement mixer of FIG. 29, in accordance with an aspect of the present invention.

Referring to FIGS. 31 and 32, the internal mechanism for a mixer powertrain base 400 is shown. Mixer base plate 401 may be rotatably connected to a mixer wind shaft 411. The mixer wind shaft 411 may be connected perpendicularly to the mixer baseplate 401, such that the mixer wind shaft 411 may have a mixer wind shaft longitudinal axis, and the mixer wind shaft 411 may rotate about the mixer wind shaft longitudinal axis. The mixer wind shaft 411, may also be connected to the mixer coil spring 402, with a first end of the mixer coil spring 402 being threaded into the mixer wind shaft 411 and the second end of the mixer coil spring 402 being connected to a mixer ground post (not shown) on the mixer baseplate 401. The washer 403 may be placed onto the mixer wind shaft 411. A mixer ratchet gear 404 may be connected to a mixer gear 405, with the mixer gear 405 and the mixer ratchet gear 404 being connected to the wind shaft 411, such that the mixer gear 405, the mixer ratchet gear 404, and the mixer wind shaft 411 are rotationally fixed with respect to each other, but are rotatable about the wind shaft longitudinal axis. A mixer shaft 412 may be connected to the paddle drive shaft 406, with the mixer shaft 412 and the paddle drive shaft 406 being connected to and rotationally fixed with respect to the mixer gear 405, the mixer ratchet gear 404, and the mixer wind shaft 411 but rotatable about wind shaft longitudinal axis.

Figure 33:
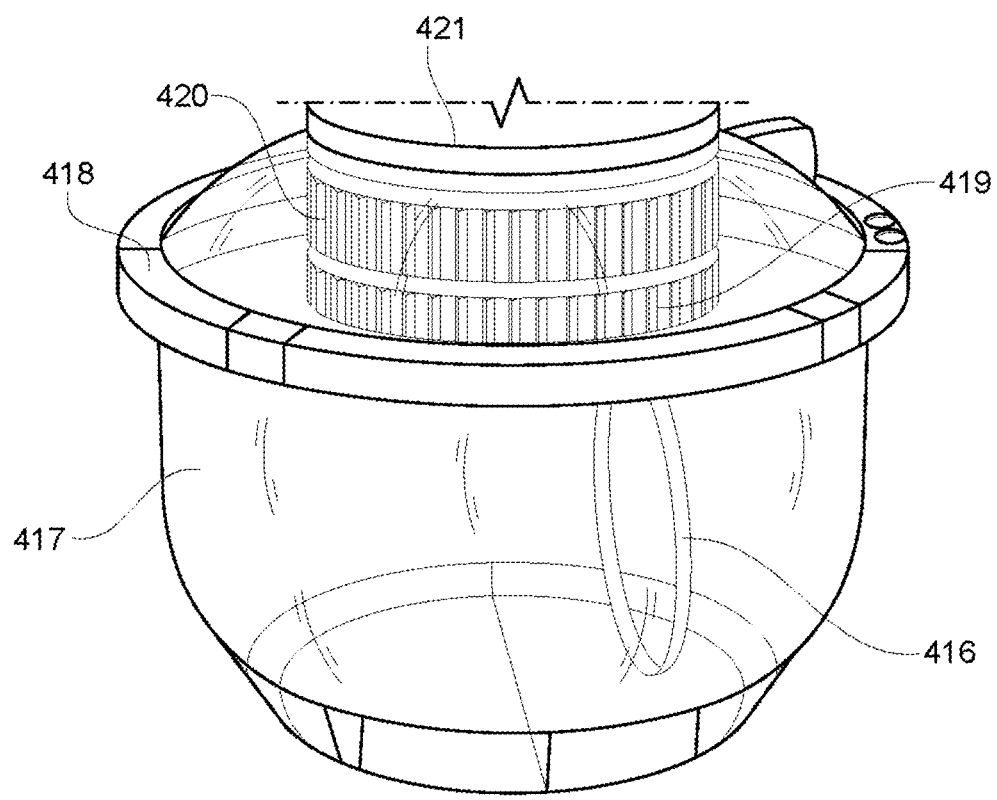
FIG. 33 is a perspective view of a bone cement mixer mixing bowl, in accordance with an aspect of the present invention.

Referring to FIG. 33, a mixing bowl 417 having a paddle 416, and a mixing bowl closure 418 are shown. The mixing bowl closure may have an internal gearing system 419, collar engagement grooves 420, and a paddle shaft aperture 421.

Referring generally to FIGS. 30-33, in some embodiments, the mixing bowl 417 may sit atop the mixer powertrain base 400, with the collar engagement grooves 420 connected to the collar 423. In other embodiments, the mixing bowl 417 may rest on a surface with the collar engagement grooves 420 being on top, with the collar 423 engaged with the collar engagement grooves 420 and the mixer baseplate 401 being on top of the powertrain base 400. Mixing bowl 417 may be connected so that paddle 416 may be connected to the paddle drive shaft 406.

There may be other embodiments of bone cement mixer that may just have a bushing (not shown) connected to the mixer ratchet gear 404 and the mixer wind shaft 411, rather than the mixer gear 405. There may also be embodiments where multiple gears are used to adjust the mixer speed, using a powertrain similar to the centrifuge 100. There may also be embodiments where the mechanical motor may be replaced with a battery and DC motor, where the DC motor rotor shaft may be directly connected to the paddle drive shaft 406.

The centrifuge 100 and centrifuge 350, may be, for example, single use, sterile, and self-powered devices. In addition, such devices may also be disposable or recyclable. For centrifuge 100, the presence of the base holes 201 may be used, for example, to wind and lock the powertrain 120, assess performance, and to help sterilize the interior. Any openings within the powertrain base 300 may, for example, be similarly used to sterilize the rotational mechanism 310 and interior of the powertrain base 300. centrifuge 100 and/or centrifuge 350 may be, for example, assembled in a clean-room. There may be, for example, bioburden and cleaning control for all components. Individual parts and/or the assembled centrifuge may undergo, for example, ethylene oxide sterilization or gamma sterilization. The devices may then be sealed and packaged. After sterilization, the centrifuge 100 may be delivered in a sealed container or packaging and with a pre-wound coil spring. Similarly, after sterilization, the centrifuge 350 may be delivered in a sealed container or packaging. The device may be opened in a sterile environment and made available for use in the sterile environment. This obviates the need for leaving the sterile environment to obtain PRP. However, other embodiments may provide for multi-use devices.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The disclosure has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the disclosure be construed as including all such modifications and alterations.

What is claimed is:

1. A method of centrifugation comprising;
providing a portable centrifuge comprising
a housing including a rotational mechanism, a trigger slot, a circuit and a housing top surface, the rotational mechanism comprising a longitudinal axis;
a centrifugal container including a bottom surface and a drive shaft connector, the centrifugal container being disposed onto the housing, at least a portion of the bottom surface of the centrifugal container contacting the housing top surface, the drive shaft connector being removably engaged to the rotational mechanism to allow the centrifugal container to be rotatable about the longitudinal axis; and
a protective cover, the protective cover comprises a trigger tab;
removing the protective cover;
introducing a fluid into the centrifugal container;
disposing the protective cover onto the centrifugal container after fluid introduction;
activating the rotational mechanism;
separating the fluid into one or more constituent components by rotation of the centrifuge; and
extracting the one or more constituent components.

2. The method of claim 1, wherein the rotational mechanism rotates the centrifugal container at rotational speeds of at least 3000 rotations per minute.

3. The method of claim 1, wherein the fluid introduced comprises blood or bone marrow.

4. The method of claim 1, wherein the one or more constituent components include at least one of red blood cells, platelet rich plasma, and platelet poor plasma.

5. The method of claim 1, wherein the centrifugal container or the protective cover comprises a polymer.

6. The method of claim 5, wherein the polymer comprises a transparent or opaque material.

7. The method of claim 1, wherein the portable centrifuge is sterilizable and a single use device.

8. The method of claim 1, wherein the longitudinal axis of the rotational mechanism extends through at least a portion of the centrifugal container.

9. The method of claim 1, wherein the portable centrifuge further comprises a direct current (DC) power source.

10. The method of claim 1, wherein the method further comprises removing the protective cover after separating the fluid into one or more constituent components.

11. The method of claim 1, wherein the protective cover comprises a conical shape.

12. The method of claim 1, wherein the step of activating rotational mechanism comprises:
inserting the trigger tab of the protective cover through the trigger slot to engage with a switch; and
rotating the protective cover relative to the centrifugal container and about the longitudinal axis from a first position to a second position to complete the circuit to activate the rotational mechanism.

13. The method of claim 12, wherein the rotating of the protective cover relative to the centrifugal container comprises a clockwise rotation about the longitudinal axis.

14. The method of claim 1, wherein the housing of the portable centrifuge further comprises a timer.

15. The method of claim 14, wherein the step of activating the rotational mechanism activates the timer.

16. The method of claim 14, wherein the timer comprises a time period of at least 1 minute.

17. The method of claim 14, wherein the timer comprises a time period range from 1 to 3 minutes.

18. The method of claim 1, wherein the extracting the one or more constituent components comprises extracting through a port opening on the protective cover or the centrifugal container.

* * * * *